US012773415B2

(12) United States Patent
Hung

(10) Patent No.: US 12,773,415 B2
(45) Date of Patent: Oct. 27, 2026

(54) METHOD FOR TREATING CANCER USING HUMAN MITOCHONDRIAL MALIC ENZYME 2 INHIBITOR

(71) Applicant: National Chung Hsing University, Taichung City (TW)

(72) Inventor: Hui-Chih Hung, Taichung City (TW)

(73) Assignee: National Chung Hsing University, Taichung City (TW)

( * ) Notice: Subject to any disclaimer, the term of this patent is extended or adjusted under 35 U.S.C. 154(b) by 345 days.

(21) Appl. No.: 18/423,712

(22) Filed: Jan. 26, 2024

(65) Prior Publication Data

US 2025/0120987 A1 Apr. 17, 2025

(30) Foreign Application Priority Data

Oct. 17, 2023 (TW) ................................ 112139634

(51) Int. Cl.

| | |
|---|---|
| ***A61K 31/192*** | (2006.01) |
| ***A61K 31/194*** | (2006.01) |
| ***A61K 31/60*** | (2006.01) |
| ***A61P 35/00*** | (2006.01) |
| ***A61P 35/02*** | (2006.01) |

(52) U.S. Cl.
CPC ............. *A61K 31/60* (2013.01); *A61P 35/02* (2018.01)

(58) Field of Classification Search
CPC .... A61K 31/60; A61K 31/192; A61K 31/194; A61P 35/00
See application file for complete search history.

(56) References Cited

PUBLICATIONS

Hsieh et al., A Small-Molecule Inhibitor Suppresses the Tumor-Associated Mitochondrial NAD(P)+-Dependent Malic Enzyme (ME2) and Induces Cellular Senescence, Oncotarget, vol. 6, No. 24, pp. 20084-20098 (Year: 2015).*

Ju-Yi Hsieh et al., Suppression of the human malic enzyme 2 modifies energy metabolism and inhibits cellular respiration, Communications Biology vol. 6, Article No. 548 (2023), Published: May 22, 2023.

Kun-Chi Chen, et al., Targeting human mitochondrial NAD(P)+-dependent malic enzyme (ME2) impairs energy metabolism and redox state and exhibits antileukemic activity in acute myeloid leukemia, Cell Oncol (Dordr). Oct. 2023;46(5):1301-1316. doi: 10.1007/s13402-023-00812-x. Epub Apr. 20, 2023.

* cited by examiner

*Primary Examiner* — Brenda L Coleman
(74) *Attorney, Agent, or Firm* — MUNCY, GEISSLER, OLDS & LOWE, P.C.

(57) ABSTRACT

A method for treating cancer using a human mitochondrial malic enzyme 2 inhibitor includes administering an effective amount of 4,4'-methylene-bis(3-hydroxy-2-naphthoic acid), of 5,5'-methylenedisalicylic acid, or of a salt of either of the aforesaid compounds to a cancer patient to inhibit the expression of human mitochondrial malic enzyme 2 in cancer cells and hence the energy metabolism of the cancer cells, thereby producing a cancer-treating effect.

4 Claims, 30 Drawing Sheets

Specification includes a Sequence Listing.

SEQUENCE LISTING

```
Sequence total quantity: 3
SEQ ID NO: 1            moltype = RNA  length = 21
FEATURE                 Location/Qualifiers
source                  1..21
                        mol_type = other RNA
                        organism = synthetic construct
SEQUENCE: 1
actgaagcct tcaactataa t                                        21

SEQ ID NO: 2            moltype = RNA  length = 20
FEATURE                 Location/Qualifiers
source                  1..20
                        mol_type = other RNA
                        organism = synthetic construct
SEQUENCE: 2
agttcttaca gagctactaa                                          20

SEQ ID NO: 3            moltype = RNA  length = 57
FEATURE                 Location/Qualifiers
source                  1..57
                        mol_type = other RNA
                        organism = synthetic construct
SEQUENCE: 3
ccggagttca gttacgatat catgtctcga gacattcgcg agtaactgaa ctttttt 57
```

METHOD FOR TREATING CANCER USING HUMAN MITOCHONDRIAL MALIC ENZYME 2 INHIBITOR

INCORPORATION BY REFERENCE TO AN ELECTRONIC SEQUENCE LISTING

The contents of the electronic sequence listing (sequence listing.xml; Size: 3,320 bytes; and Date of Creation: Jan. 26, 2024) is herein incorporated by reference in its entirety.

BACKGROUND OF THE INVENTION

1. Technical Field

The present invention relates to the second use of a small-molecule compound. More particularly, the invention relates to a method for treating cancer using a human mitochondrial malic enzyme 2 inhibitor.

2. Description of Related Art

Human mitochondrial NAD(P)$^+$-dependent malic enzyme 2 (hereinafter also referred to as ME2 for short) is a redox enzyme associated with such cellular metabolic reactions as glyconeogenesis, fatty acid synthesis, and energy generation. According to recent studies, ME2 is related to the growth, multiplication, or metastasis of cancer cells and tends to be expressed in cancer cells that progress relatively fast, such as those of lung cancer, skin cancer, and blood cancer. ME2, therefore, has been identified as a key enzyme that can contribute to the control or treatment of cancer.

Leukemia, also known as blood cancer, is a disease caused by cancerization of bone marrow and characterized by the proliferation of abnormal leukocytes. Leukemia can be divided by the speed of progression and the source and type of cancer cells into acute myeloid leukemia (AML), chronic myeloid leukemia, acute lymphoblastic leukemia, and chronic lymphoblastic leukemia. AML is a highly malignant and fast-progressing leukemia, clinically treated nowadays mainly by chemotherapy; however, not all patients can stand the severe discomfort of chemotherapy. Bone marrow transplantation and targeted therapy are alternatives to chemotherapy, but the relatively great difficulty in finding a suitably matched donor for marrow transplantation and the high cost of targeted therapy make it impossible for all patients to use one or the other of those alternatives.

BRIEF SUMMARY OF THE INVENTION

The primary objective of the present invention is to provide a method for treating cancer using a human mitochondrial malic enzyme 2 inhibitor. More specifically, the human mitochondrial malic enzyme 2 inhibitor disclosed herein is a novel cancer-treating, or anticancer, composition that binds to human mitochondrial NAD(P)$^+$-dependent malic enzyme 2 in cells to effectively inhibit the expression of the human mitochondrial NAD(P)$^+$-dependent malic enzyme, thereby inhibiting the ability of a cancer cell to grow and to develop in a different part of the patient's body, the goal being to provide cancer treatment and increase the survival rate of the cancer patient effectively.

To achieve the foregoing objective, the present invention discloses a method for treating cancer using a human mitochondrial malic enzyme 2 inhibitor. The method includes administering an effective amount of a small-molecule compound or of a salt thereof to a cancer patient, wherein the small-molecule compound is 4,4'-methylene-bis(3-hydroxy-2-naphthoic acid) or 5,5'-methylenedisalicylic acid.

In one embodiment of the present invention, the salt of the small-molecule compound is in the form of a sodium salt.

In another embodiment of the present invention, the small-molecule compound or the salt thereof is a human mitochondrial NAD(P)$^+$-dependent malic enzyme 2 inhibitor; that is to say, the small-molecule compound or the salt thereof can bind to human mitochondrial NAD(P)$^+$-dependent malic enzyme 2 to form a complex, thereby inhibiting the activity of human mitochondrial NAD(P)$^+$-dependent malic enzyme 2 and hence inhibiting the energy metabolism of cells.

In one embodiment of the present invention, the anticancer composition is used to treat blood cancer or lung cancer.

In one embodiment of the present invention, the aforesaid blood cancer is acute myeloid leukemia.

In one embodiment of the present invention, the anticancer composition can inhibit the growth of cancer cells, inhibit metastasis of cancer cells, or inhibit the invasion of cancer cells into other cells or organs.

DETAILED DESCRIPTION OF THE INVENTION

Figure 1:
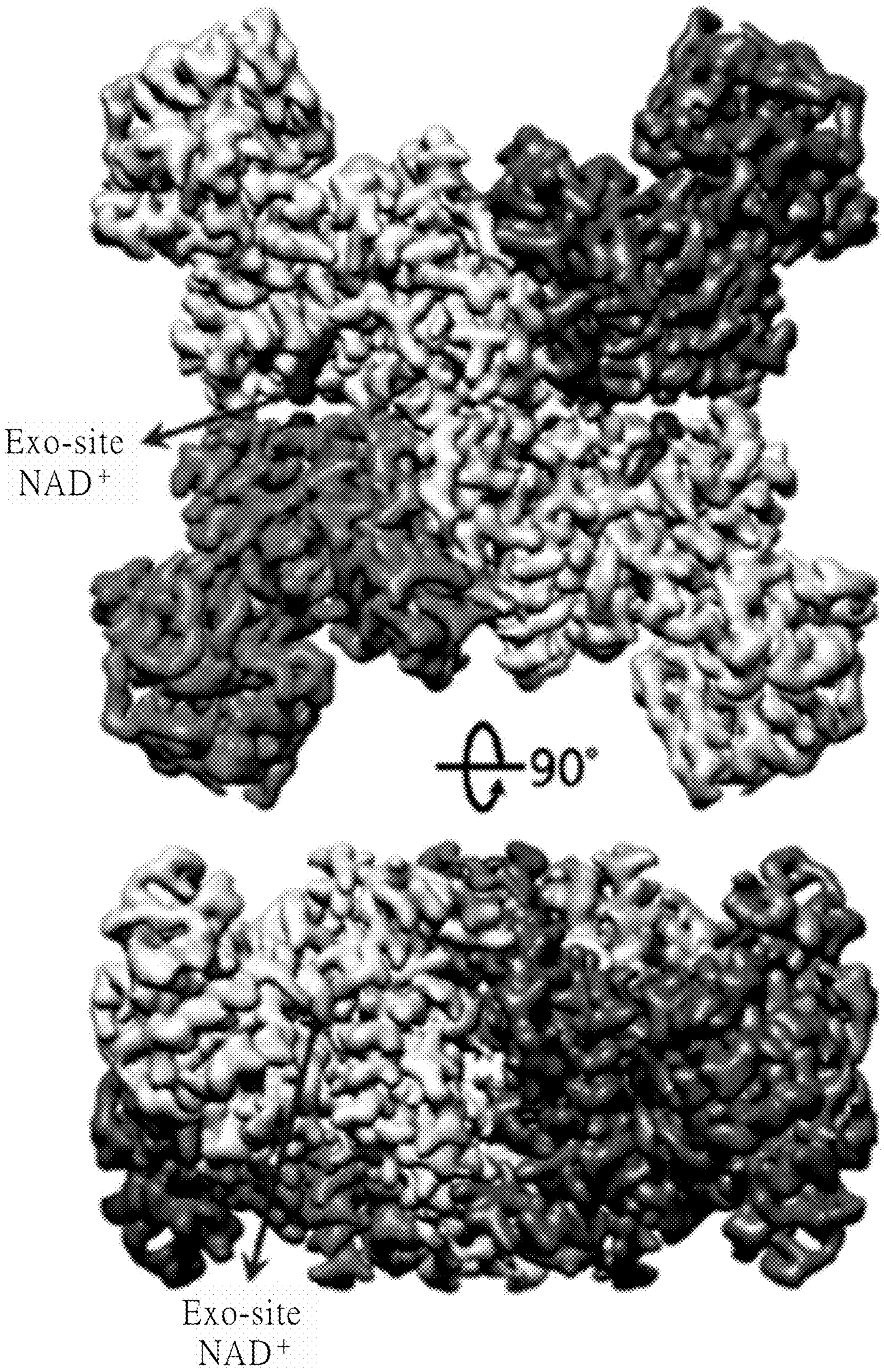
FIG. 1 shows a cryo-electron microscopic analysis result of the binary complex ME2-NAD$^+$, with the arrow indicating the exo-site NAD$^+$.

The present invention provides a method for treating cancer using a human mitochondrial malic enzyme 2 inhibitor. The method includes administering an effective amount of a small-molecule compound or of a salt thereof to a cancer patient, wherein the small-molecule compound is 4,4'-methylene-bis(3-hydroxy-2-naphthoic acid) (also known as embonic acid, or EA for short) or 5,5'-methylene-disalicylic acid (or MDSA for short).

The method disclosed herein for treating cancer using a human mitochondrial malic enzyme 2 inhibitor can effectively inhibit the expression of human mitochondrial malic enzyme 2 in an individual's cells, thereby inhibiting energy metabolism, and consequently growth and multiplication, of the cells. Therefore, the small-molecule compound disclosed herein or the salt thereof can function as the main active ingredient of an anticancer composition.

In one embodiment of the present invention, the salt of the small-molecule compound disclosed herein is a sodium salt of the small-molecule compound, such as a sodium salt of 4,4'-methylene-bis(3-hydroxy-2-naphthoic acid).

In one embodiment of the present invention, the small-molecule compound or the salt thereof can be used to inhibit the growth of cancer cells and/or inhibit metastasis of the cancer cells so as to control or slow down the progression of cancer.

In one embodiment of the present invention, the cancer to be treated is lung cancer or blood cancer, wherein the blood cancer is acute myeloid leukemia.

The EA and MDSA disclosed herein are ME2 inhibitors; in other words, each of the EA and MDSA disclosed herein can bind to an allosteric site at a dimer interface of ME2 or of a mutant thereof and thereby change the configuration, and hence inhibit the activity, of ME2. More specifically, when EA or MDSA binds to ME2 such that a complex is formed, the spatial location of the glutamic acid at position 255 of ME2 (Glu255) is altered, and so are the spatial locations of the aspartic acid at position 256 (Asp256) and of the aspartic acid at position 279 (Asp279); in addition, Asp256, which is located at side-chain position 256, is specifically substituted by the arginine at position 165 (Arg165). As Glu255, Asp256, and Asp279 are required for chelation and catalysis of the divalent ions at the active sites of ME2, the changes in spatial location caused by the binding of EA or MDSA to ME2 lead to a loss of the divalent ions at the active sites and inhibit catalysis.

Unless otherwise defined, all the technical and/or scientific terms used herein have substantially the same connotations or meanings as understood by a person who is skilled, and has common general knowledge, in the art.

Figure 2:
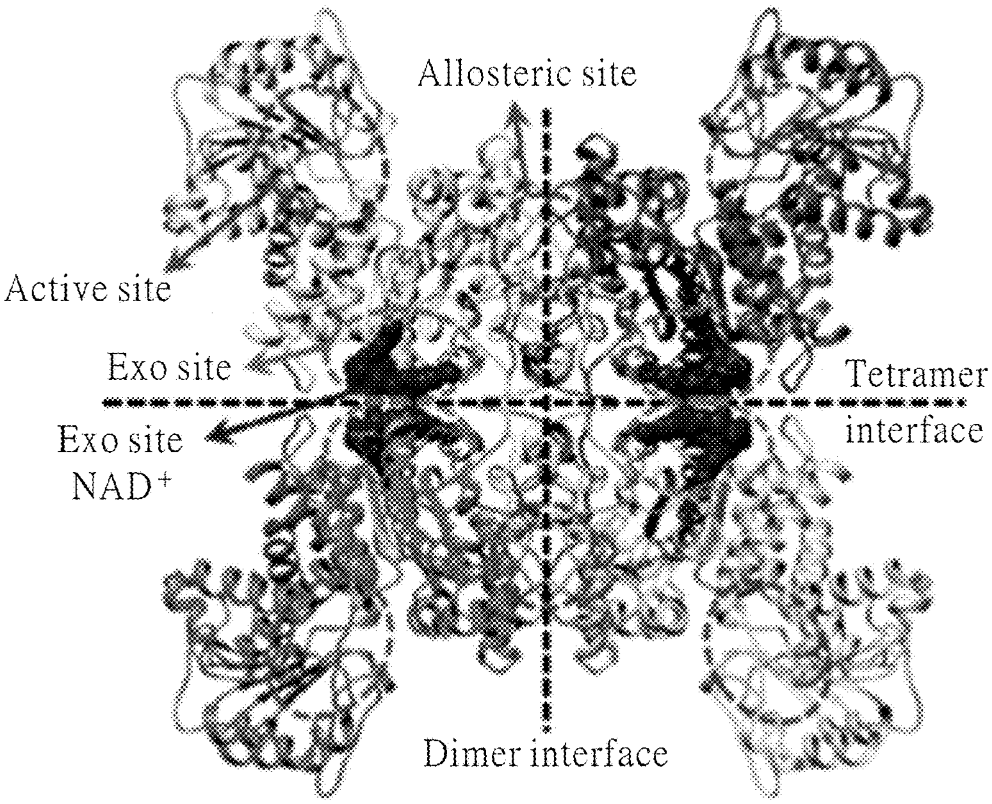
FIG. 2 shows a further cryo-electron microscopic analysis result of the complex ME2-NAD$^+$.

The term "ME2 (human mitochondrial NAD(P)$^+$-dependent malic enzyme 2)" refers to an isoform of malic enzyme, and as revealed by cryo-electron microscopy (cryo-EM), ME2 has the structure shown in FIG. 1 and FIG. 2. It can be seen in FIG. 1 and FIG. 2 that ME2 is different from the other malic enzyme isoforms mainly in that ME2 has dual cofactor specificity and a complicated allosteric regulatory system, and that a fumarate can bind to the allosteric sites of ME2 as an activator to control the activity of ME2. More specifically, ME2 catalyzes the oxidation of malate in a cell and reduces NAD$^+$ or NADP$^+$ to pyruvate and NADH or NADPH. Therefore, when the activity of the ME2 in a cell is inhibited, the generation of pyruvate and NADH or NADPH in the cell will be affected.

The term "mutant of ME2" refers to that which is obtained by altering, replacing, removing, or substituting at least one amino acid in the amino acid sequence of ME2 in a natural or artificial manner.

The term "malic enzyme" (or ME for short) refers to a new enzyme for oxidative decarboxylation. Malic enzyme can convert L-malate into pyruvate while reducing NAD(P)$^+$ to NAD(P)H. The malic enzyme in mammals can be divided by subcellular localization and cofactor specificity into three isoforms: ME1, ME2, and ME3, which have different physiological functions.

The term "ME2 inhibitor" refers to an allosteric inhibitor of human ME2 that can reduce the activity of ME2 effectively. The ME2 inhibitor disclosed herein may be a disalicylic acid derivative, a naphthoic acid derivative, a pharmaceutically acceptable salt of either of the aforesaid compounds, or a composition whose main active ingredient is either of the aforesaid compounds or a salt thereof.

Figure 3:
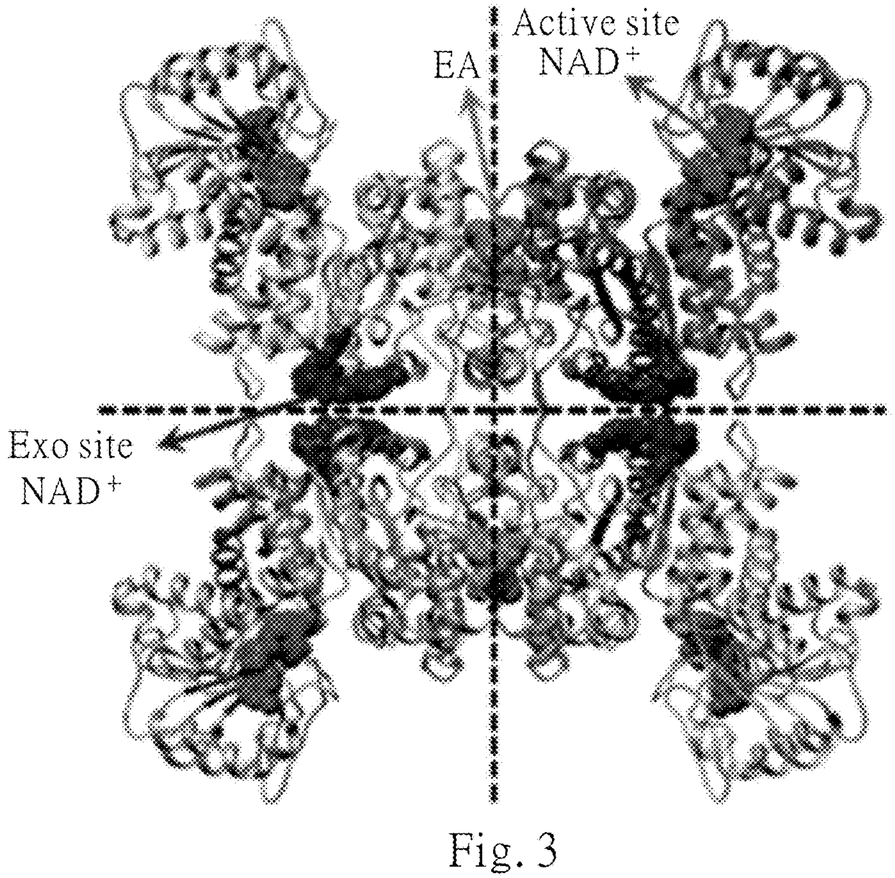
FIG. 3 shows a cryo-electron microscopic analysis result of the complex ME2-EA.
Figure 4:
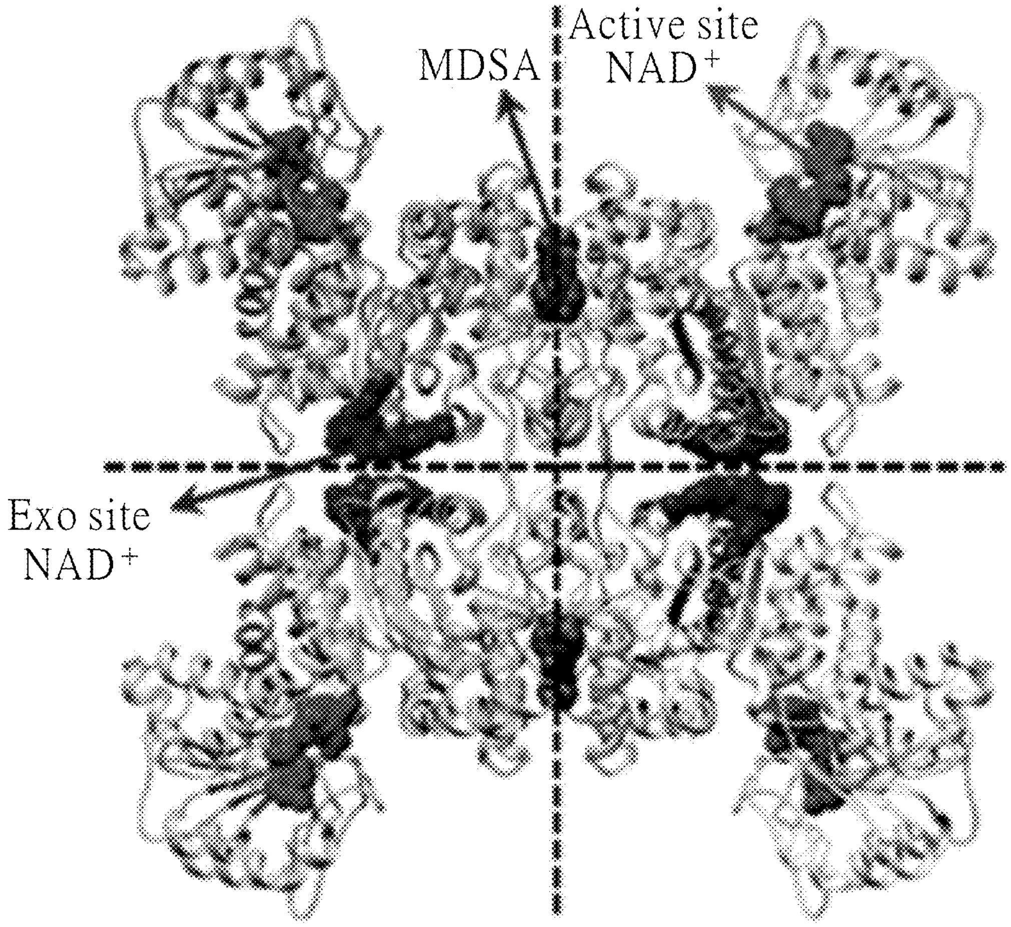
FIG. 4 shows a cryo-electron microscopic analysis result of the binary complex ME2-MDSA.

The term "EA (embonic acid)" refers to 4,4'-methylenebis(3-hydroxy-2-naphthoic acid), which is a naphthoic acid derivative that can bind to an allosteric site of ME2 to form the complex ME2-EA, as shown in FIG. 3.

The term "MDSA" refers to 5,5'-methylenedisalicylic acid, which is a disalicylic acid derivative that can bind to an allosteric site of ME2 to form the complex ME2-MDSA, as shown in FIG. 3.

The term "$Na_2EA$ (disodium embonate)" refers to a sodium salt of EA. It is another allosteric inhibitor of human ME2 as disclosed herein.

The term "therapeutically effective amount" or "effective amount" refers to an amount in which a compound or a pharmaceutically acceptable salt thereof is administered and that can alleviate one or more symptoms of the disease to be treated, reduce the discomfort of one or more symptoms of the disease, or slow down the progression of the disease.

The term "treating" refers to reversing, alleviating, or inhibiting the progression, or one or more symptoms, of the disease to which the term is applied or preventing the occurrence of the disease to which the term is applied or of complications thereof. The term "treatment" refers to a therapeutic action of "treating" as defined herein.

The term "acute myeloid leukemia" (or AML for short) refers to a blood cancer caused mainly by the proliferation of immature hematopoietic cells in bone marrow or blood, wherein the proliferation interferes with hematopoiesis and keeps normal blood cells from performing their physiological functions.

To better demonstrate the technical features and effects of the present invention, a detailed description of some examples is given below with reference to the accompanying drawings.

Unless otherwise stated, the biological materials used in the following examples such as cells and vectors are easily obtainable by a person with common general knowledge in the art.

The H1299 cells (human non-small-cell lung cancer cells) and MCF-7 cells (human breast cancer cells) used in the following examples were both verified to be able to express ME2. The MCF-7 cells were cultured in separate Dulbecco's modified Eagle's media (DMEM) each containing 10% fetal bovine serum and 1% penicillin/streptomycin, and the H1299 cells in separate RPMI culture media (HyClone™) each containing 10% fetal bovine serum and 1% penicillin/streptomycin. All the culture environments were at 37° C. and contained 5% carbon dioxide.

All the AML cell strains used in the following examples, i.e., HL-60 cells, THP-1 cells, MV4-11 cells, and OCI-AML-2 cells, were verified to be able to express ME2. The HL-60 cells, THP-1 cells, MV4-11 cells, and OCI-AML-2 cells were cultured in separate RPMI-1640 culture media each added with 10% fetal bovine serum and 1% penicillin/streptomycin. All the culture environments were at 37° C. and contained 5% carbon dioxide.

The animal test in the following examples complied with relevant ethical regulations on animal experiments. The animal test in the examples was used to verify the effects of the disclosed technical features of the present invention but not to limit the scope of the present description or the appended claims. The present description and the appended claims should be interpreted according to common general knowledge in the art. For example, the doses used for the experimental animals in the examples were not intended to limit the disclosed technical features of the invention. A person skilled in the art will be able to calculate the doses for different species of animals based on common general knowledge.

Example 1: Preparation of ME1 and ME2

The PRH281 vector, which is controlled by the trp promoter, was used to transcribe the gene of human ME2 protein to *Escherichia coli* BL21, and IAA (indol-3-acetic acid) was used to induce the expression of human ME2 protein by the *E. coli* BL21. The ME2 protein was subsequently obtained by way of purification.

Similarly, pET21b, which is controlled by the T7 promoter, was used to transcribe the gene of human ME1 protein to *E. coli* BL21, and IPTG (isopropyl-D-1-thiogalactopyranoside) was used to induce the expression of human ME1 protein by the *E. coli* BL21. The ME1 protein was subsequently obtained by way of purification.

Example 2: Test on ME2 Inhibition

Each of EA (a naphthoic acid derivative) and MDSA (a disalicylic acid derivative) was added into a reaction buffer through a titration process in order to analyze the inhibition effect of each compound on ME1 and ME2.

In the ME1 inhibition test, the reaction buffer used contained 50 mM Tris-HCl (7.4), 15 mM L-malate, 0.2 mM $NAD^+$, and 10 mM $MgCl_2$.

In the ME2 inhibition test, the reaction buffer used contained 50 mM Tris-HCl (7.4), 40 mM L-malate, 2 mM $NAD^+$, and 10 mM $MgCl_2$.

In each inhibition test, the titration concentrations of EA and MDSA were in the range from 0 to 40 μM, and the titration concentrations of salicylic acid, 3-benzoyl-benzoic acid, 3,5-dihydroxy-2-naphthoic acid, 3,7-dihydroxy-2-naphthoic acid, 7-bromo-3-hydroxy-2-naphthoic acid, 1-hydroxy-2-naphthoic acid, 3-hydroxy-2-naphthoic acid, and 2,6-dicarboxy naphthalene were in the range from 0 to 500 μM.

Referring to the test results shown in Table 1, EA, MDSA, 3,5-dihydroxy-2-naphthoic acid, 1-hydroxy-2-naphthoic acid, and 3-hydroxy-2-naphthoic acid were relatively effective in inhibiting the activity of ME2. EA and MDSA, in particular, were the most effective in inhibiting the activity of ME2.

TABLE 1

Half maximal inhibitory concentrations ($IC_{50}$) of various compounds with respect to ME2

| Compound | $IC_{50}$ (μM) |
|---|---|
| EA | 0.51 |
| MDSA | 1.1 |
| Salicylic acid | 800.7 |
| 3-benzoyl-benzoic acid | 652 |
| 3,5-dihydroxy-2-naphthoic acid | 12.4 |
| 7-bromo-3-hydroxy-2-naphthoic acid | 307.8 |
| 3,7-dihydroxy-2-naphthoic acid | 37.6 |
| 1-hydroxy-2-naphthoic acid | 74.7 |
| 3-hydroxy-2-naphthoic acid | 105.4 |
| 2,6-dicarboxy naphthalene | 352.9 |

Example 3: Sensitivity Test

16 ME2 mutants were designed by way of biotechnology. The $IC_{50}$ values of EA and MDSA with respect to each ME2 mutant were determined in the same way as in example 2, and the results are shown in Table 2.

TABLE 2

$IC_{50}$ of EA and MDSA with respect to 16 ME2 mutants

| Code of ME2 mutant | Description of mutation design | $IC_{50}$ of MDSA (μM) | $IC_{50}$ of EA (μM) |
|---|---|---|---|
| WT | No mutation | 0.51 ± 0.03 | 1.14 ± 0.05 |
| N35A | Asparagine at position 35 was changed to alanine. | 237.8 ± 24.5 | 84.0 ± 4.6 |
| N35D | Asparagine at position 35 was changed to aspartic acid. | 20.1 ± 2.0 | 10.4 ± 1.1 |
| N35Q | Asparagine at position 35 was changed to glutamine. | 510.5 ± 29.2 | 189.7 ± 4.8 |
| K57A | Lysine at position 57 was changed to alanine. | 0.57 ± 0.07 | 0.31 ± 0.03 |
| K57S | Lysine at position 57 was changed to serine. | 0.26 ± 0.03 | 0.69 ± 0.09 |
| E59A | Glutamic acid at position 59 was changed to alanine. | 0.25 ± 0.08 | 1.93 ± 0.18 |
| E59N | Glutamic acid at position 59 was changed to asparagine. | 0.50 ± 0.05 | 3.32 ± 0.19 |
| Q64A | Glutamine at position 64 was changed to alanine. | 18.0 ± 1.8 | 8.27 ± 1.06 |
| Q64E | Glutamine at position 64 was changed to glutamic acid. | 91.8 ± 4.6 | 41.2 ± 3.7 |
| Q64N | Glutamine at position 64 was changed to asparagine. | 62.4 ± 5.4 | 38.2 ± 4.4 |
| R67Q | Arginine at position 67 was changed to glutamine. | 184.5 ± 9.45 | 15.14 ± 1.66 |
| R91A | Arginine at position 91 was changed to alanine. | 2.89 ± 0.23 | 8.13 ± 0.56 |
| N92A | Asparagine at position 92 was changed to alanine. | 3.53 ± 0.72 | 6.66 ± 0.37 |
| N92Q | Asparagine at position 92 was changed to glutamine. | 1.28 ± 0.17 | 1.77 ± 0.13 |
| R128A | Arginine at position 128 was changed to alanine. | 2.30 ± 0.32 | 5.25 ± 0.38 |
| Y562A | Tyrosine at position 562 was changed to alanine. | 40.8 ± 5.0 | 46.1 ± 2.5 |

It can be inferred from the results in Table 2 that the glutamine at position 64 (Glu64) and the tyrosine at position 562 (Tyr562) are important to the binding of EA or MDSA to ME2, and that mutations at the other positions have no impact on the binding of EA or MDSA to ME2. In other words, the MDSA or EA disclosed herein can bind to mutants of ME2 to form complexes and thereby inhibit the activity of those ME2 mutants.

Example 4: Analysis of the Effect of EA or MDSA on the Metabolic Pathways of Cancer Cells (1)

H1299 cells ($3\times10^5$ cells) were cultured for 24 hours in separate culture media each containing 20 mM L-malate, with the culture environment being at 37° C. and containing 5% carbon dioxide. The cells were then treated separately with 25 μM EA or MDSA for 48 hours. After that, the cultured cells in each group were collected and were centrifuged in 100 μL of phosphate buffer, and the supernatants were collected. Once the proteins in the supernatants were removed, a pyruvate colorimetric/fluorometric assay kit and a PicoProbe™ NADPH quantification fluorometric assay kit were used to analyze the pyruvate content and NADPH content of the cells respectively (Ex/Em: at 535 nm and 587 nm). The assay results are shown in FIG. 5 and FIG. 6, in which EA represents cell groups treated with EA while MDSA represents cell groups treated with MDSA.

Figure 5:
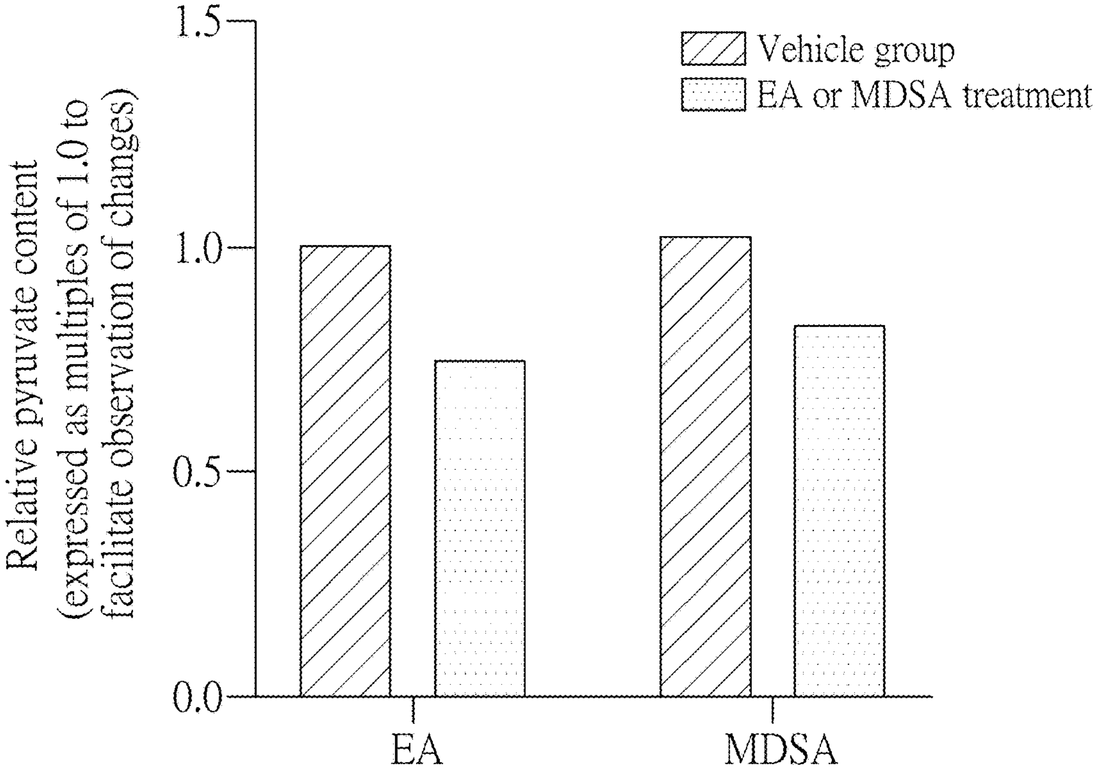
FIG. 5 shows an analysis result of changes in the pyruvate contents of EA or MDSA-treated H1299 cells.
Figure 6:
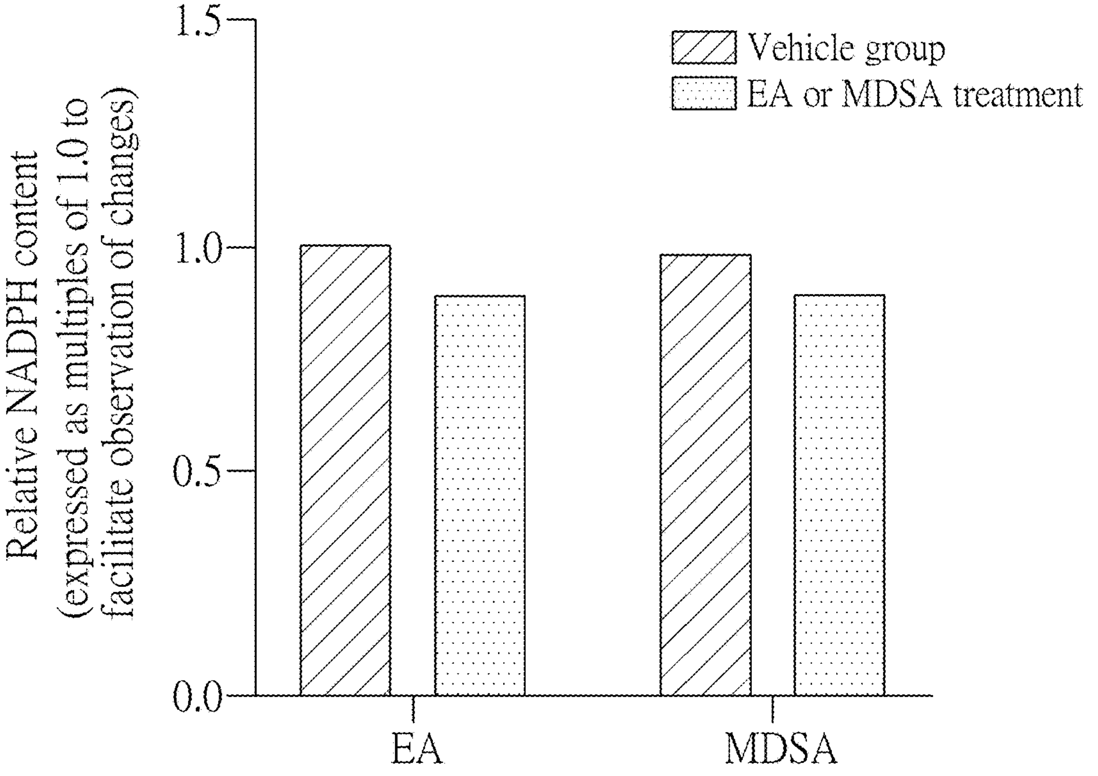
FIG. 6 shows an analysis result of changes in the NADPH contents of EA or MDSA-treated H1299 cells.

It can be inferred from the results in FIG. 5 and FIG. 6 that EA and MDSA can reduce the pyruvate content and NADPH content of H1299 cells respectively. This indicates that EA and MDSA can inhibit the activity of the ME2 in cancer cells and thereby change ME2-related metabolism in the cells, causing death of the cancer cells due to a reduction in the pyruvate content and the NADPH content.

In addition, MCF-7 cells ($6\times10^5$ cells) were cultured in the same way as the H1299 cells and had their pyruvate content and NADPH content analyzed. The analysis results show that the pyruvate content and NADPH content of the EA or MDSA-treated MCF-7 cells were not reduced significantly.

It can be known from the foregoing results that while both H1299 cells and MCF-7 cells can express ME2, MCF-7 cells are insensitive to EA or MDSA. This indicates that the EA and MDSA disclosed herein have specificity in treating particular cancers.

Example 5: Analysis of the Effect of EA or MDSA on the Metabolic Pathways of Cancer Cells (2)

Figure 7:
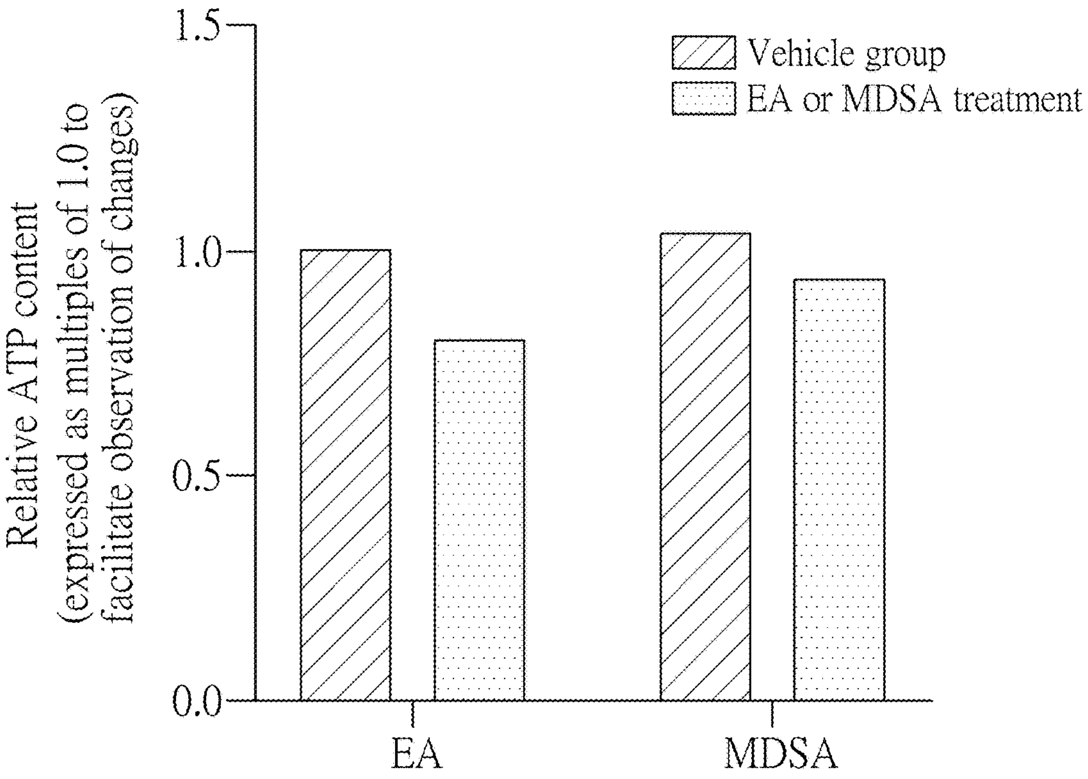
FIG. 7 shows an analysis result of changes in the ATP contents of EA or MDSA-treated H1299 cells.
Figure 8:
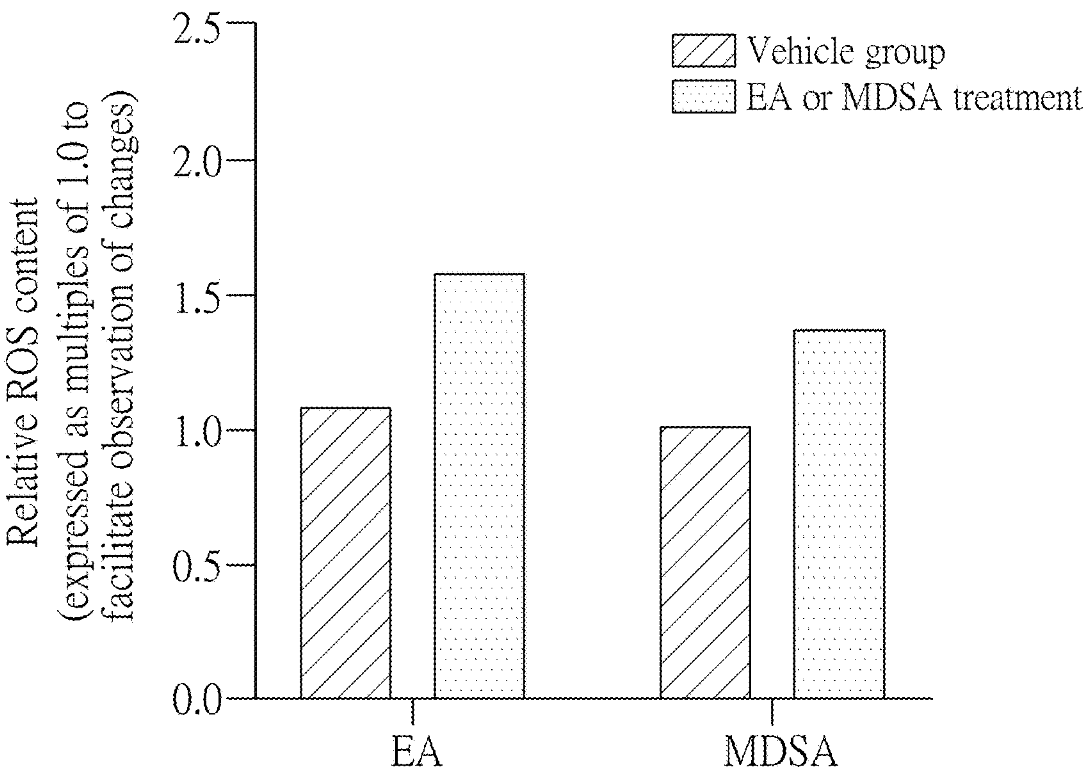
FIG. 8 shows an analysis result of changes in the ROS contents of EA or MDSA-treated H1299 cells.
Figure 9:
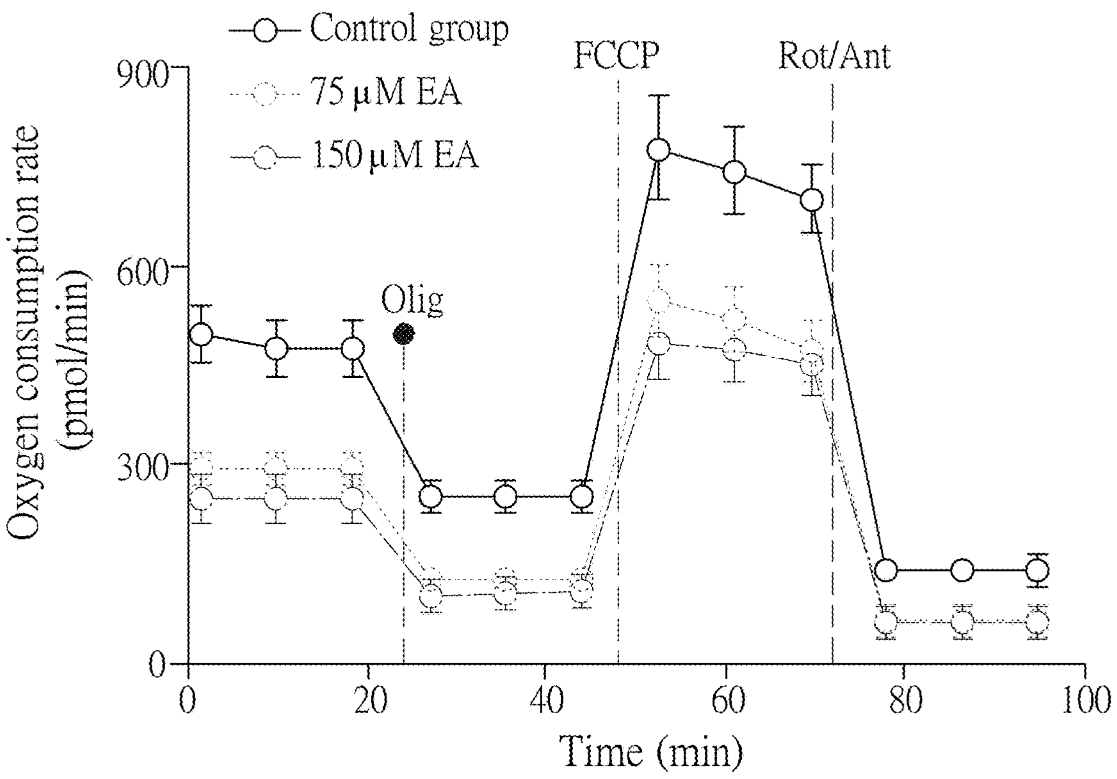
FIG. 9 shows an analysis result of changes in the oxygen consumption rates of H1299 cells treated with EA of different concentrations.
Figure 10:
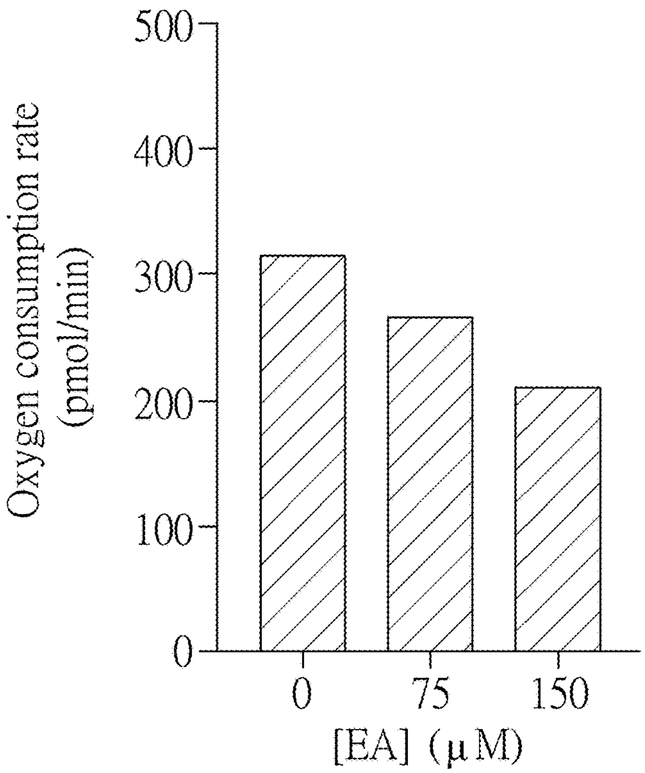
FIG. 10 shows an analysis result of the basal respiration rates of the H1299 cells in FIG. 9.
Figure 11:
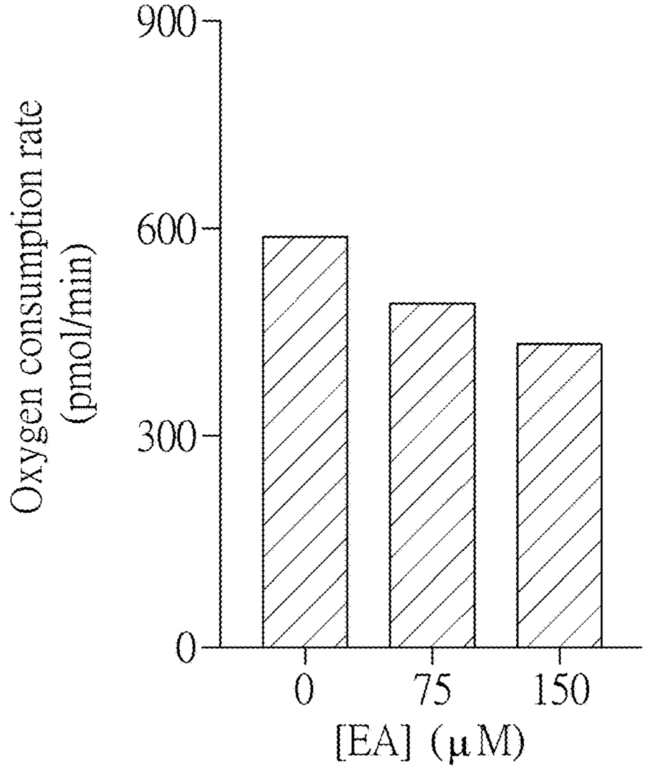
FIG. 11 shows an analysis result of the maximum respiration rates of the H1299 cells in FIG. 9.
Figure 12:
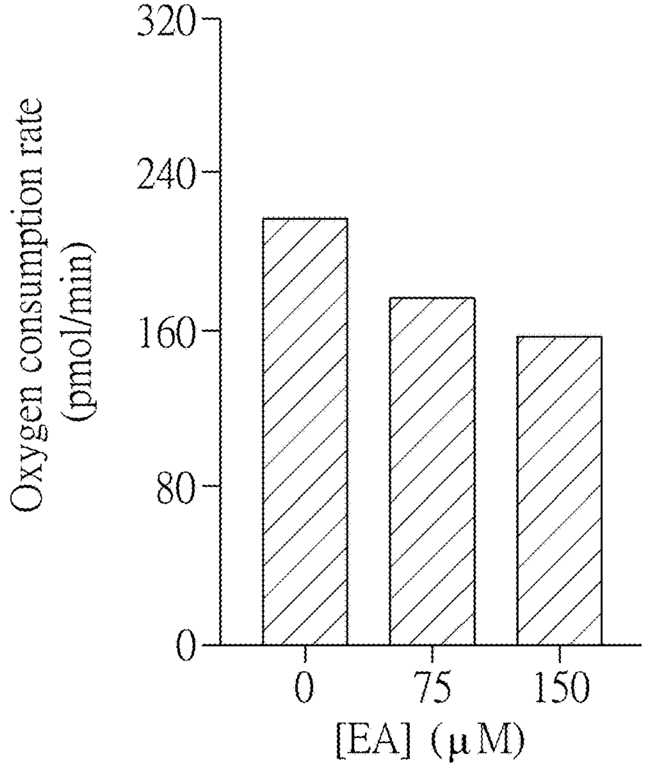
FIG. 12 shows an analysis result of the generation of ATP by the mitochondrial electron transport chains in the H1299 cells in FIG. 9.
Figure 13:
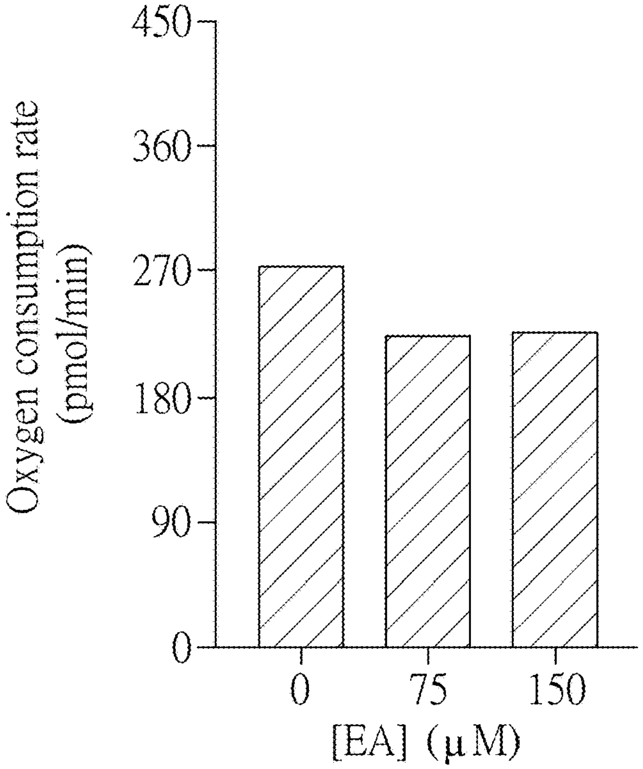
FIG. 13 shows an analysis result of the spare respiratory capacity of the H1299 cells in FIG. 9.
Figure 14:
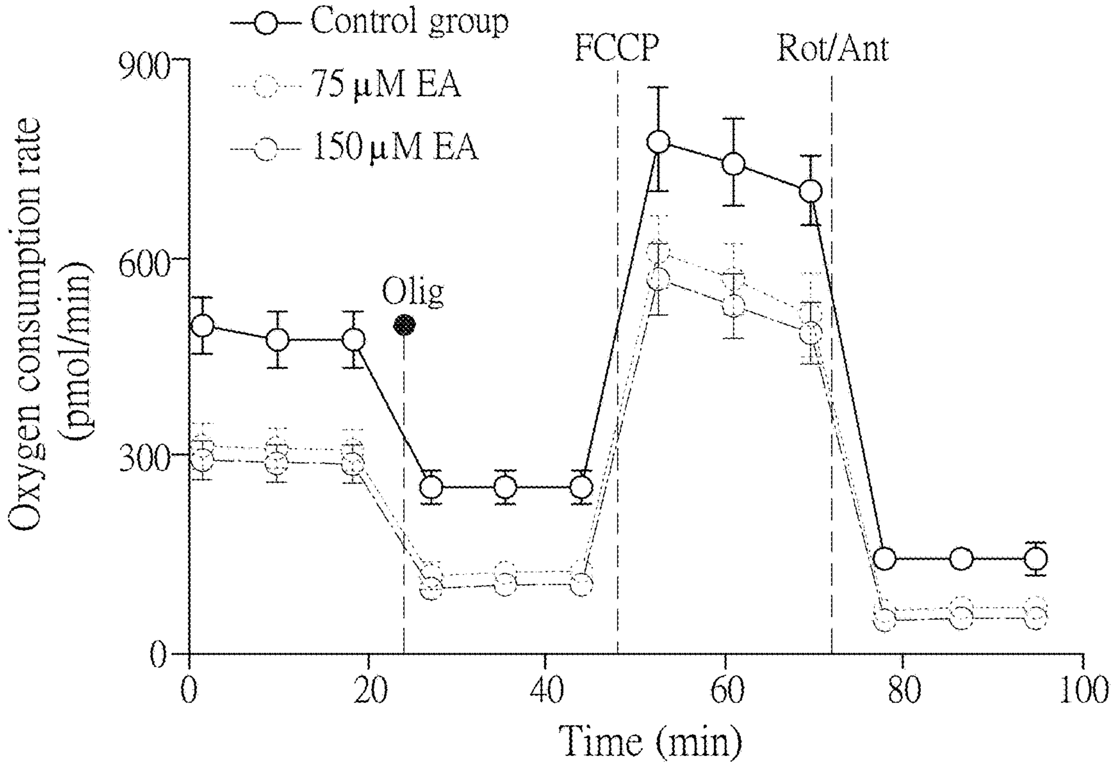
FIG. 14 shows an analysis result of changes in the oxygen consumption rates of H1299 cells treated with MDSA of different concentrations.
Figure 15:
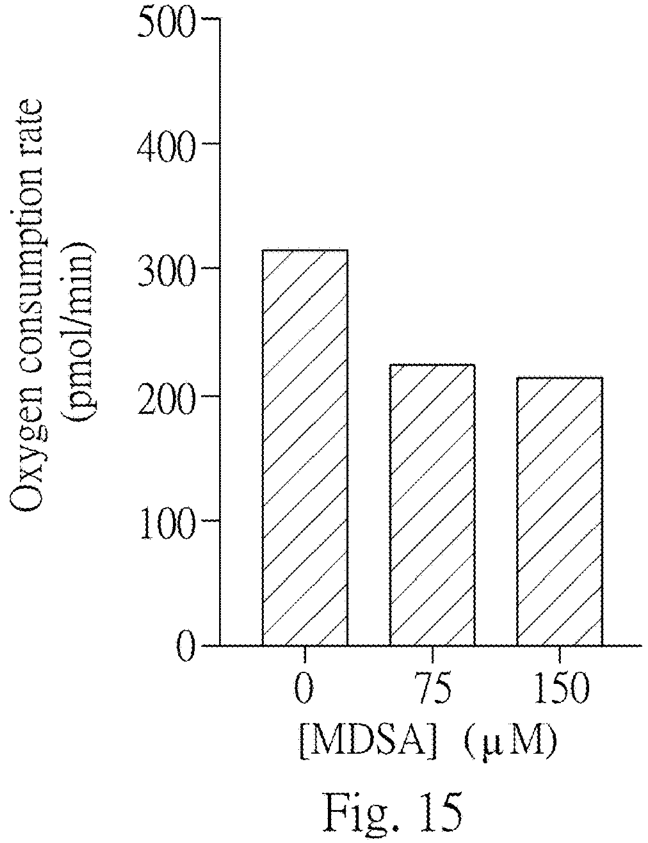
FIG. 15 shows an analysis result of the basal respiration rates of the H1299 cells in FIG. 14.
Figure 16:
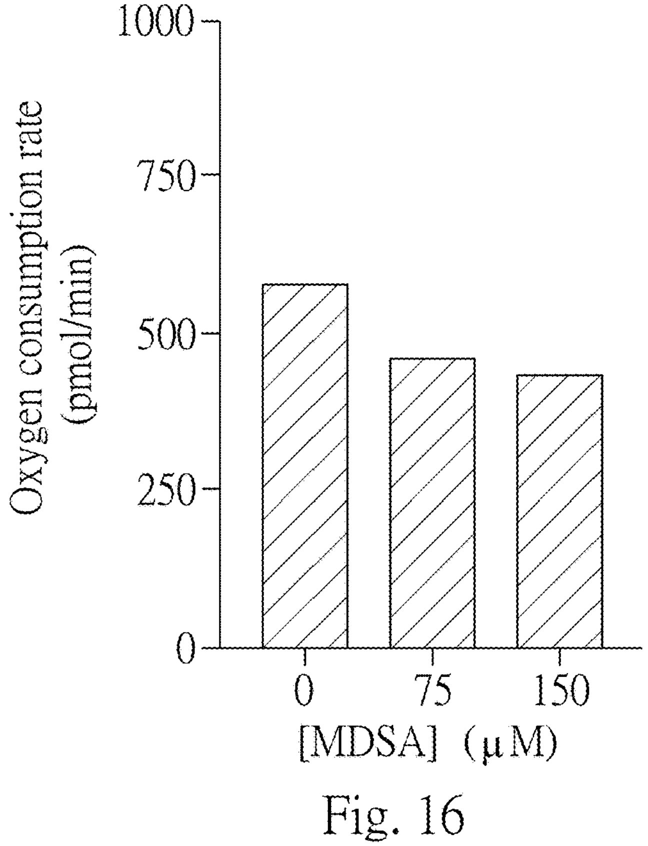
FIG. 16 shows an analysis result of the maximum respiration rates of the H1299 cells in FIG. 14.
Figure 17:
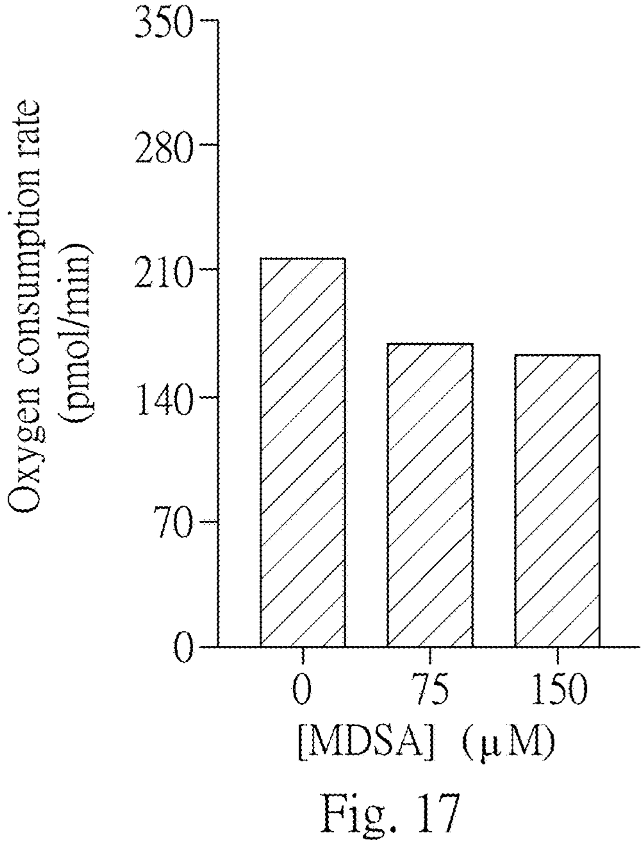
FIG. 17 shows an analysis result of the generation of ATP by the mitochondrial electron transport chains in the H1299 cells in FIG. 14.
Figure 18:
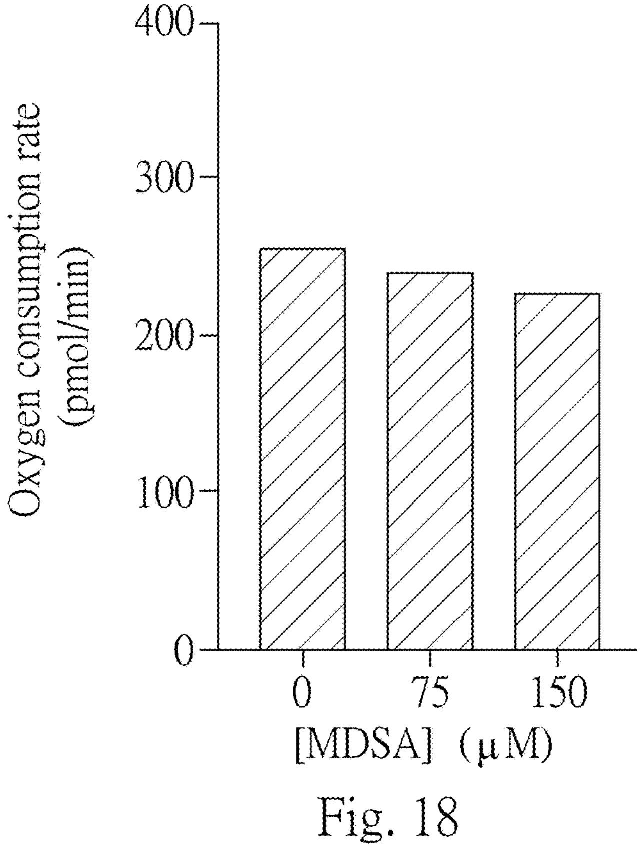
FIG. 18 shows an analysis result of the spare respiratory capacity of the H1299 cells in FIG. 14.

H1299 cells ($3\times10^5$ cells) were cultured in separate culture media each containing 20 mM L-malate. Each culture medium was also added with 150 μM EA or MDSA. After culturing for 48 hours in a culture environment that was at 37° C. and contained 5% carbon dioxide, a cell viability assay kit (CellTiter-Glo® 2.0 Cell Viability Assay Kit) was used to analyze the ATP contents of the cells, and the results are shown in FIG. 7. Also, a ROS assay kit (#cat.MAK143, Sigma-Aldrich, St. Louis, MO, USA) was used to analyze the ROS contents of the cells, and the results are shown in FIG. 8. In the bar charts of FIG. 7 and FIG. 8, EA represents cell groups treated with EA, and MDSA represents cell groups treated with MDSA.

In can be inferred from the results in FIG. 7 and FIG. 8 that EA and MDSA can lower the ATP contents, and increase the ROS contents, of H1299 cells. This indicates that EA and MDSA can cause a reduction in energy generation, and an increase in oxidative stress, in cancer cells by inhibiting the activity of the ME2 in the cancer cells, thereby leading to death of the cancer cells.

Example 6: Cell Activity Test

An Agilent Seahorse XF24 cell culture microplate was inoculated with H1299 cells ($1.75\times10^4$ cells), and the cells were cultured in a 5% carbon dioxide and 37° C. environment for 24 hours. The H1299 cells were then exposed separately to 0, 75, and 150 μM EA or MDSA for 3 hours. After that, the cells were cultured for 30 minutes in a 37° C. environment that did not contain carbon dioxide, and the growth media were changed to basic culture media each containing 1 mM pyruvate, 4 mM glutamine, and 1 mg/mL D-glucose. The cells were subsequently treated with 5 μM oligomycin A (abbreviated as Olig in FIG. 9 and FIG. 14), 2 μM FCCP (carbonyl cyanide 4-(trifluoromethoxy)phenylhydrazone), and 1 μM ronstone/antinomycin A (abbreviated as Rot/Ant in FIG. 9 and FIG. 14), in that order, at a 24-minute interval. Finally, a Seahorse XFe24 analyzer was used to perform a Seahorse XF cell mito stress test on the cells to obtain the oxygen consumption rates (OCR) of the cells, and the test results are shown in FIG. 9 to FIG. 18. The control groups were formed by cells to which no EA or MDSA was added.

The results in FIG. 9 to FIG. 13 show that the basal respiration rates, maximum respiration rates, ATP generation, and spare respiratory capacity of the H1299 cells induced with EA were all reduced. The results in FIG. 14 to FIG. 18 show that the basal respiration rates, maximum respiration rates, and ATP generation of the H1299 cells induced with MDSA were lowered, too. This indicates that the cell respiration rates of lung cancer cells can be reduced by EA or MDSA inhibiting the activity of the ME2 in the lung cancer cells. That is to say, the EA or MDSA disclosed herein can effectively cause death, or a loss of activity, of lung cancer cells, thereby producing the intended effect of treating, or slowing down the progression of, cancer.

This example also included culturing MCF-7 cells ($2.8\times10^4$ cells) in the same way as the H1299 cells and determining the oxygen consumption rates of the cultured MCF-7 cells, and the test results show that the basal respiration rates, maximum respiration rates, ATP generation, and spare respiratory capacity of the MCF-7 cells, be they treated with EA or MDSA, remained the same. This indicates that the EA and MDSA disclosed herein have therapeutic specificity toward particular cancers.

Example 7: Cell Migration Assay

A 24-well plate was inoculated with H1299 cells ($1.5\times10^5$ cells) and MCF-7 cells ($3.0\times10^5$ cells), and the cells were cultured in a 37° C. and 5% carbon dioxide environment for 24 hours in order for a confluent monolayer of cells to be formed. After that, the culture medium was removed, and the cells were washed with a phosphate buffer. A score, or wound, was then made in the monolayer of cells, and the cells were treated with 150 μM EA or MDSA for 48 hours in a 37° C. and 5% carbon dioxide environment. Cell migration was observed under an automated microscope, and a quantitative analysis of cells was performed at the same time. The analysis results are shown in FIG. 19 to FIG. 22.

Figure 19:
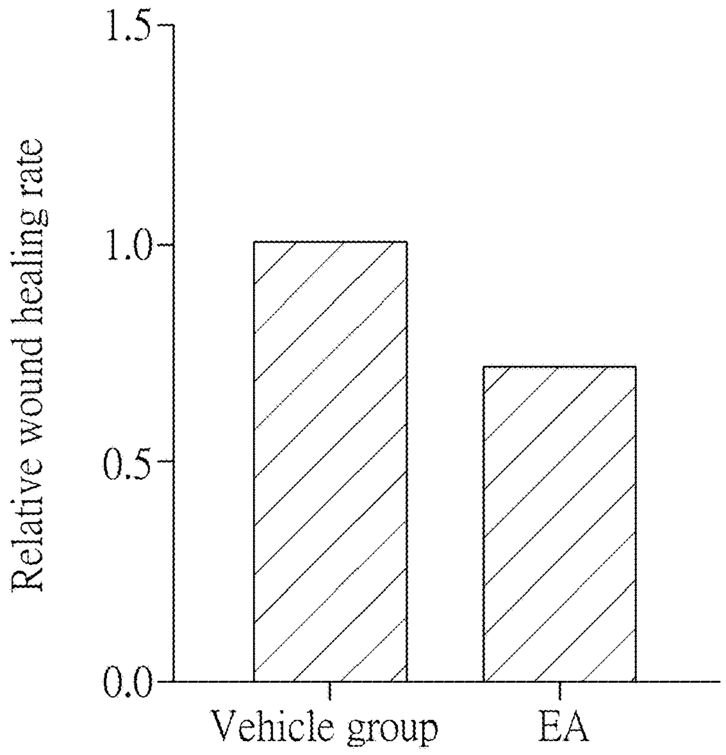
FIG. 19 shows the quantification result of a wound healing assay of EA-treated H1299 cells.
Figure 20:
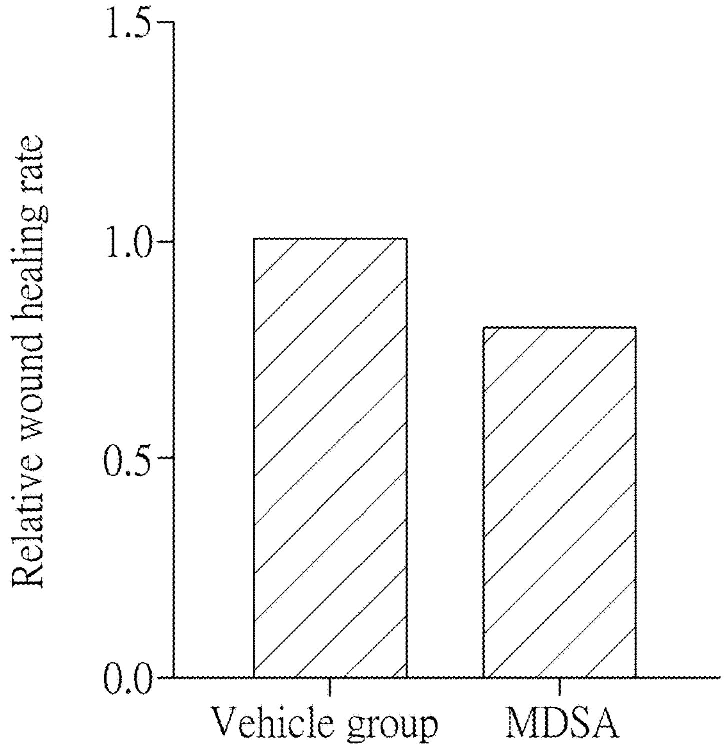
FIG. 20 shows the quantification result of a wound healing assay of MDSA-treated H1299 cells.
Figure 21:
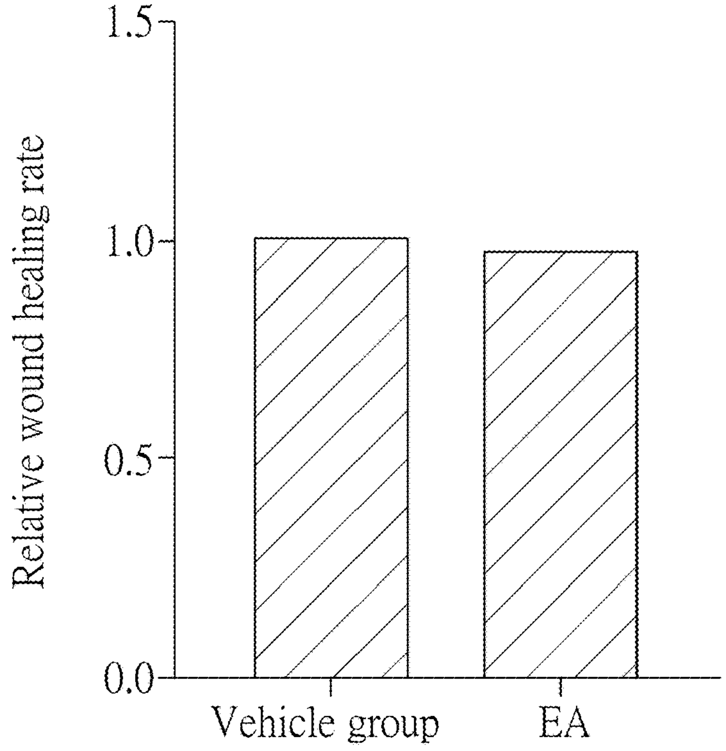
FIG. 21 shows the quantification result of a wound healing assay of EA-treated MCF-7 cells.
Figure 22:
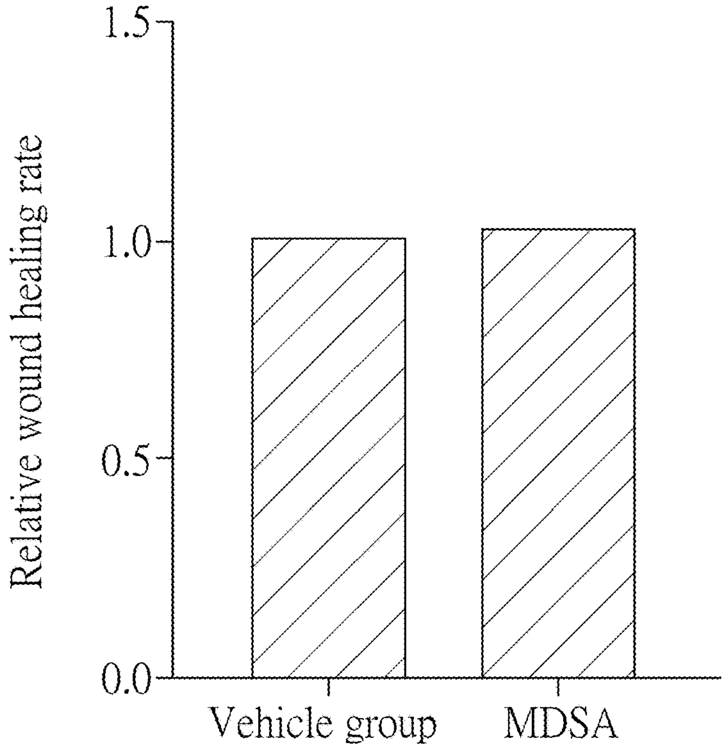
FIG. 22 shows the quantification result of a wound healing assay of MDSA-treated MCF-7 cells.

It can be inferred from the results in FIG. 19 and FIG. 20 that EA and MDSA can inhibit the migration of H1299 cells, and it can be further inferred from the results in FIG. 21 and FIG. 22 that EA and MDSA cannot inhibit the migration of MCF-7 cells.

Example 8: Cell Invasion Assay

The walls of the upper chambers of a 24-well plate (Transwell®) were coated with a culturing gel (Matrigel®) and left in the coated state for 24 hours, wherein the culturing gel had been diluted with a culture medium that did not contain fetal bovine serum, with the concentration of the culturing gel for H1299 cells being 1000 μg/mL, and the concentration of the culturing gel for MCF-7 cells being 200 μg/mL. The upper chambers were then inoculated with H1299 cells ($1.0\times10^5$ cells) and MCF-7 cells ($1.5\times10^5$ cells), and the cells were treated with 150 μM EA or MDSA for 24 hours. A culture medium containing 10% fetal bovine serum was subsequently added to the lower chambers. After that, cell invasion was observed with an inverted microscope, and cell quantification was performed at the same time. The results are shown in FIG. 23 to FIG. 26. The vehicle groups, which were formed by cells to which no EA or MDSA was added, were provided to enable the calculation of the amount of the cells in each EA or MDSA-treated group in relation to the amount of the cells in the corresponding vehicle group at the end of the assay so that changes in the relative amounts of cells can be observed with ease.

Figure 23:
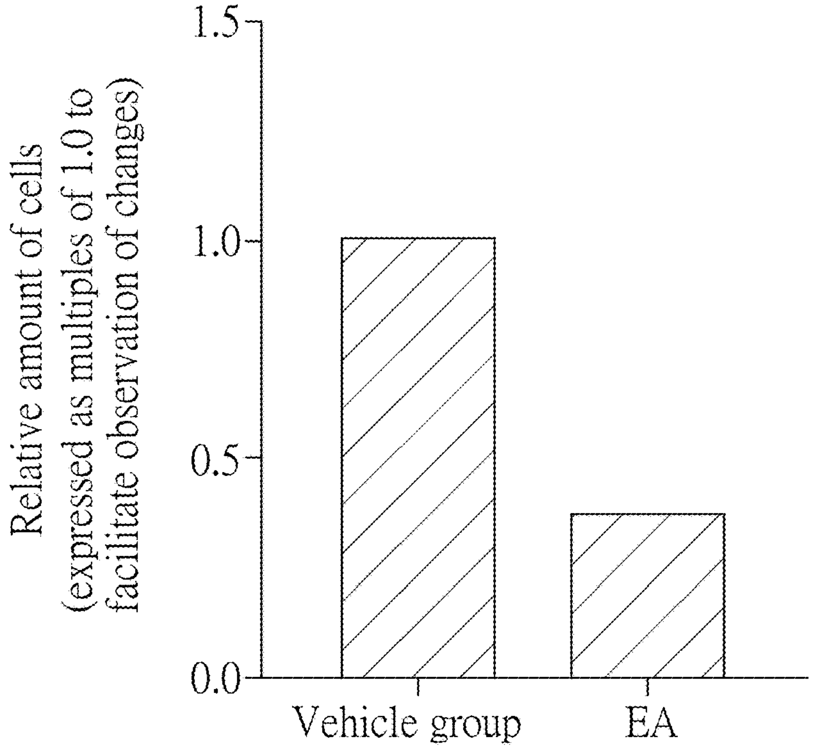
FIG. 23 shows the quantification result of a cell invasion assay of EA-treated H1299 cells.
Figure 24:
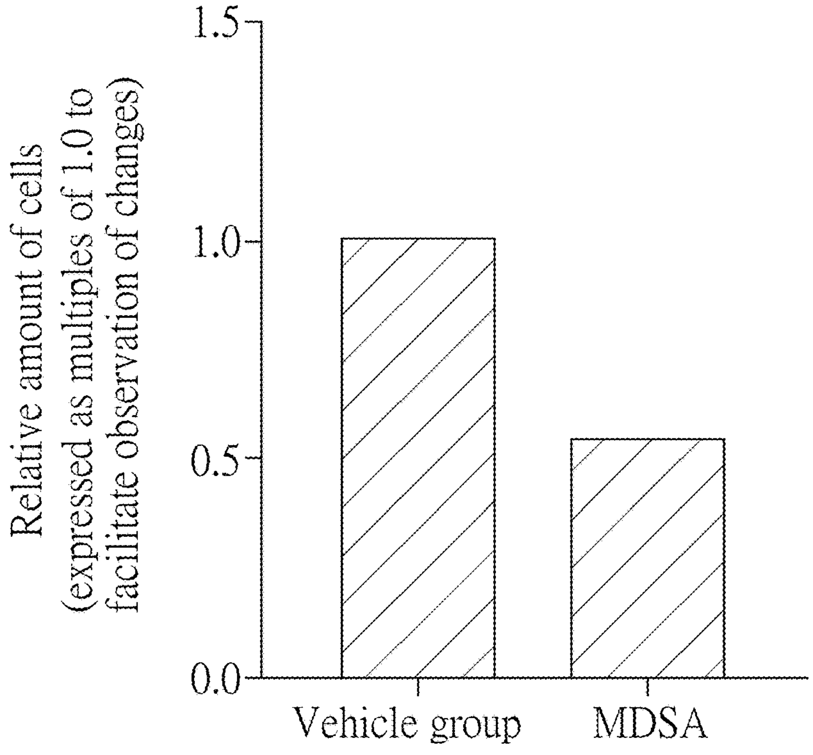
FIG. 24 shows the quantification result of a cell invasion assay of MDSA-treated H1299 cells.
Figure 25:
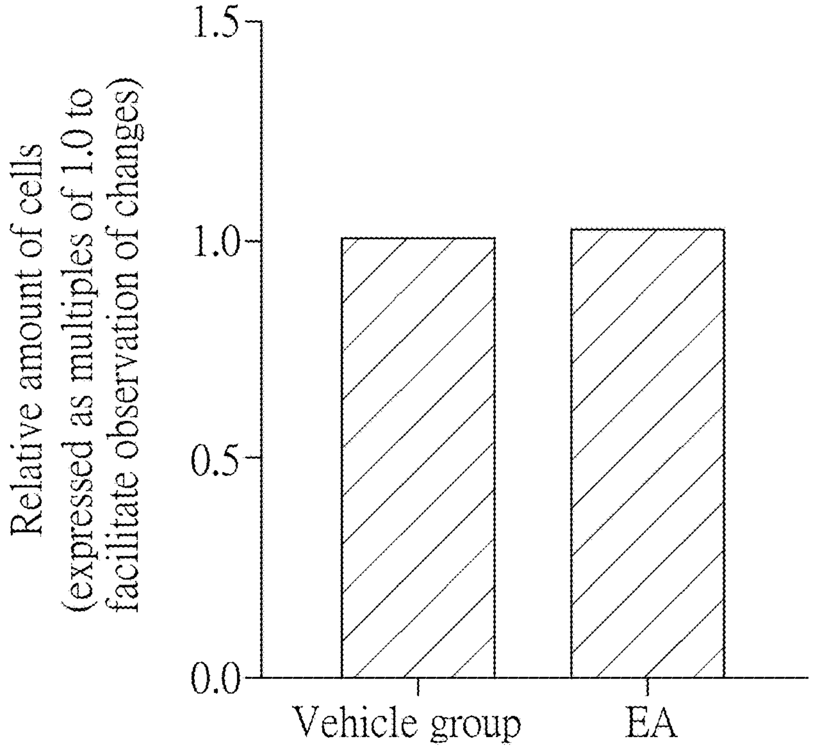
FIG. 25 shows the quantification result of a cell invasion assay of EA-treated MCF-7 cells.
Figure 26:
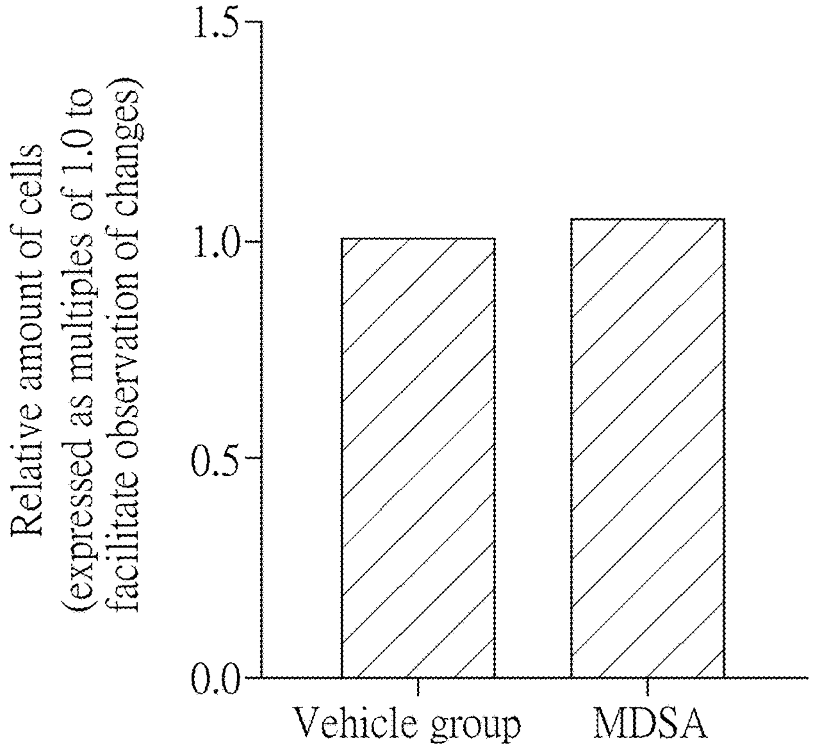
FIG. 26 shows the quantification result of a cell invasion assay of MDSA-treated MCF-7 cells.

It can be inferred from the results in FIG. 23 and FIG. 24 that EA and MDSA can inhibit the invasion of H1299 cells, and it can be further inferred from the results in FIG. 25 and FIG. 26 that EA and MDSA cannot inhibit the invasion of MCF-7 cells.

Example 9: Analysis of the Relation Between the Activity of AML Cells and the Expression of ME2

The two shRNA sequences shME2-1 (SEQ ID No.: 1) and shME2-2 (SEQ ID No.: 2) were transfected separately into HL-60 cells, THP-1 cells, and MV4-11 cells to silence the ME2 gene in those AML cells, and the sequence shCtrl (SEQ ID No.: 3) was transfected into other HL-60, THP-1, and MV4-11 cells to form the control-group cells. The AML cells whose ME2 gene had been knocked out by the different shRNA sequences and the normal AML cells were cultured separately for 24 hours in Petri dishes each containing an RPMI culture medium. After that, the culture media were renewed, and the cells were cultured for another 48 hours, before a commercially available apoptosis detection kit (Annexin V Apoptosis Detection Kit) and flow cytometer were used to analyze the apoptosis rates of the cells. The analysis results are shown in FIG. 27.

Figure 28:
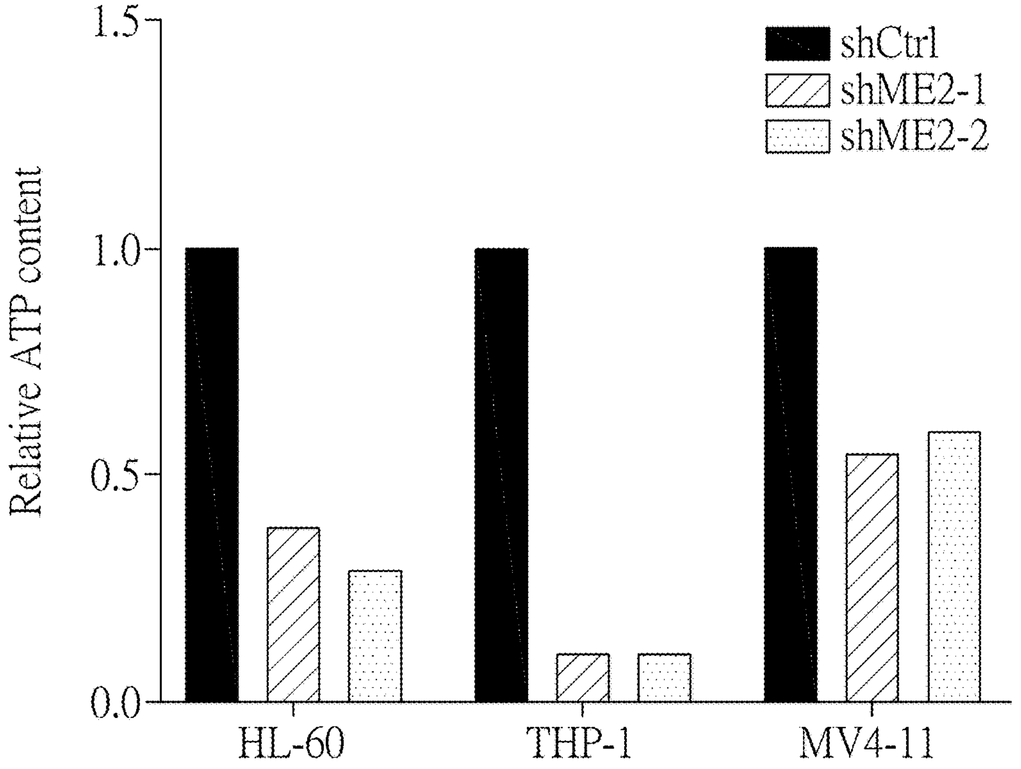
FIG. 28 shows an analysis result of the relative amounts of the ATP generated in AML cells whose ME2 gene has been knocked out and in normal AML cells.
Figure 29:
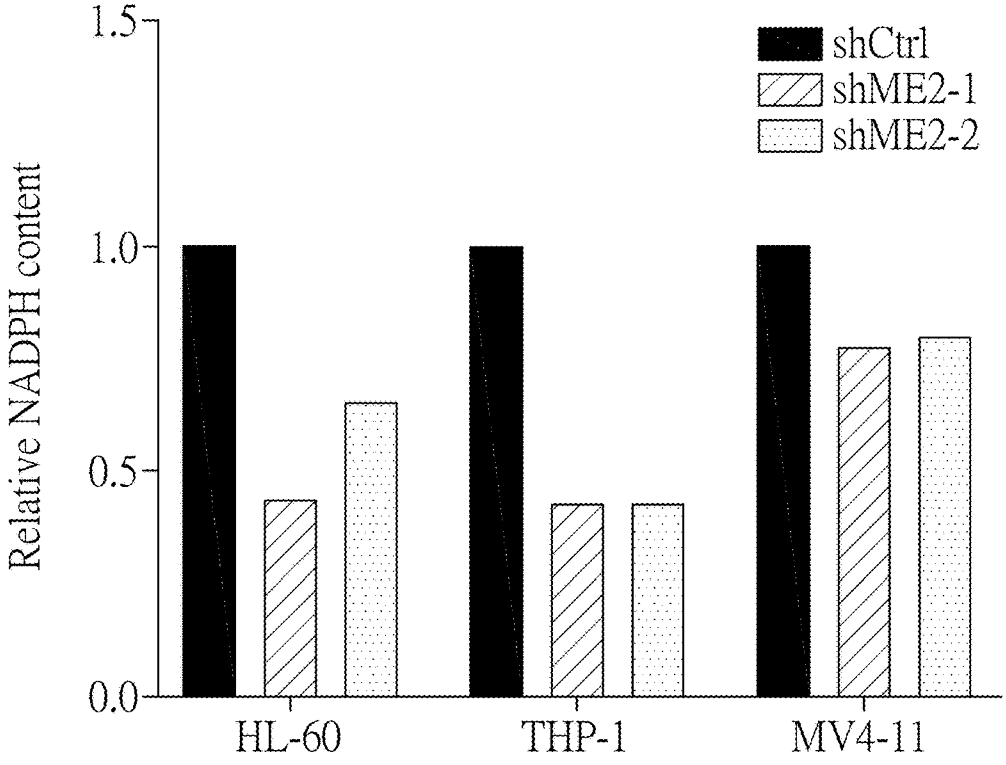
FIG. 29 shows an analysis result of the NADPH contents of AML cells whose ME2 gene has been knocked out and of normal AML cells.
Figure 30:
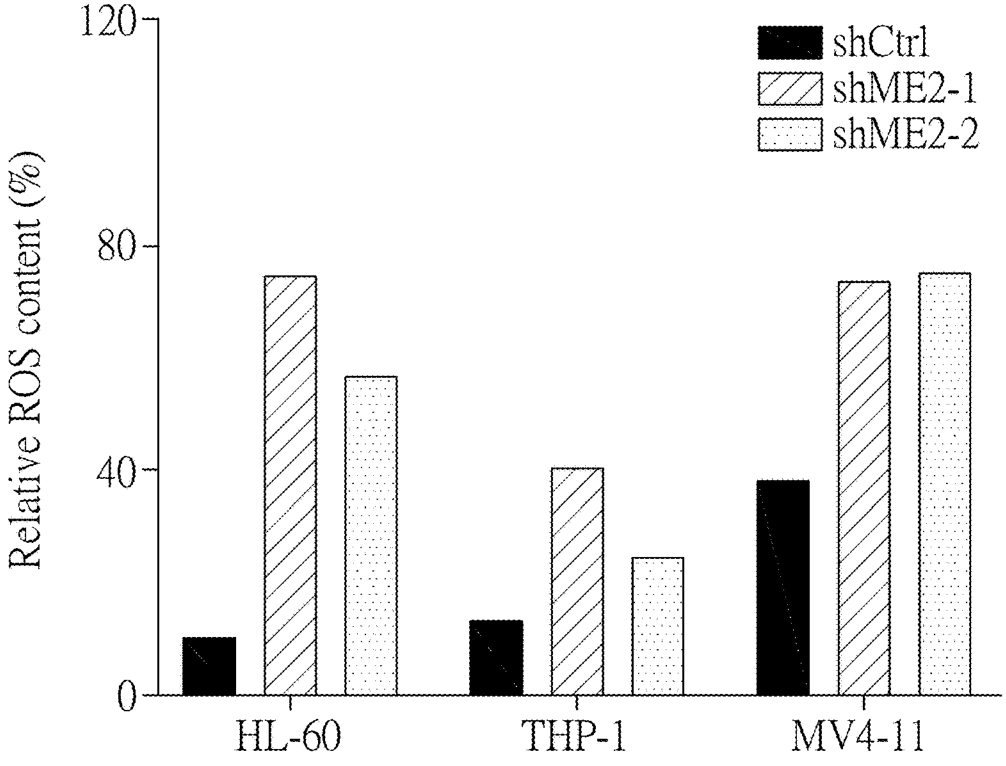
FIG. 30 shows an analysis result of the ROS contents of AML cells whose ME2 gene has been knocked out and of normal AML cells.
Figure 31:
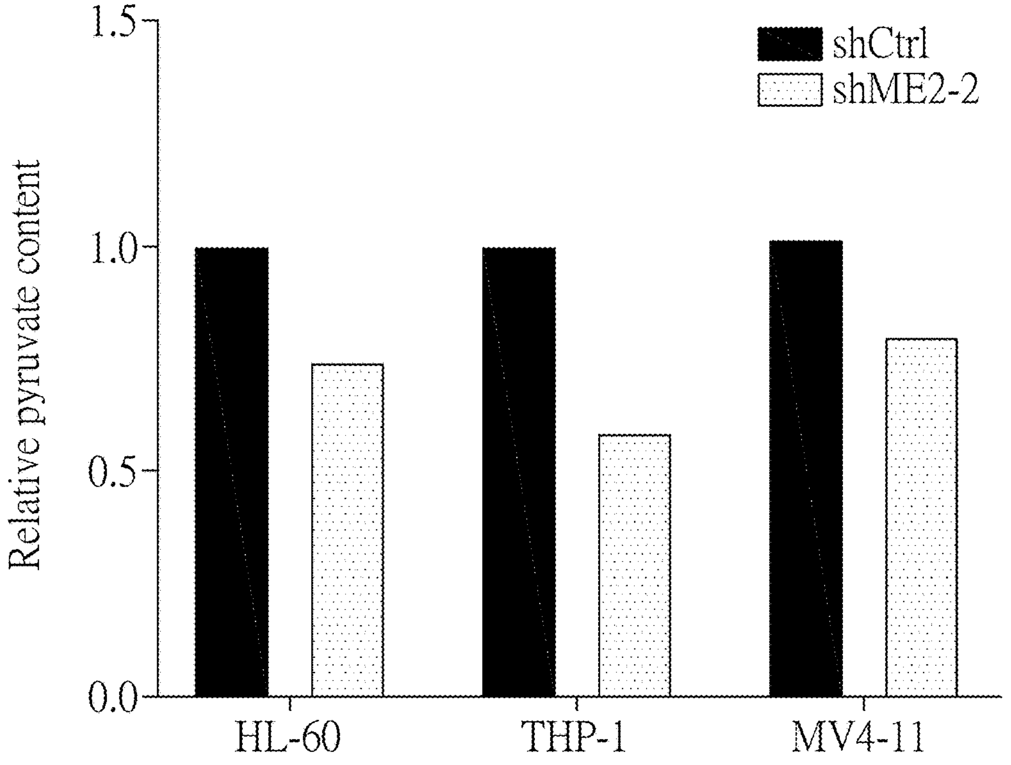
FIG. 31 shows an analysis result of the pyruvate contents of AML cells whose ME2 gene has been knocked out and of normal AML cells.
Figure 32:
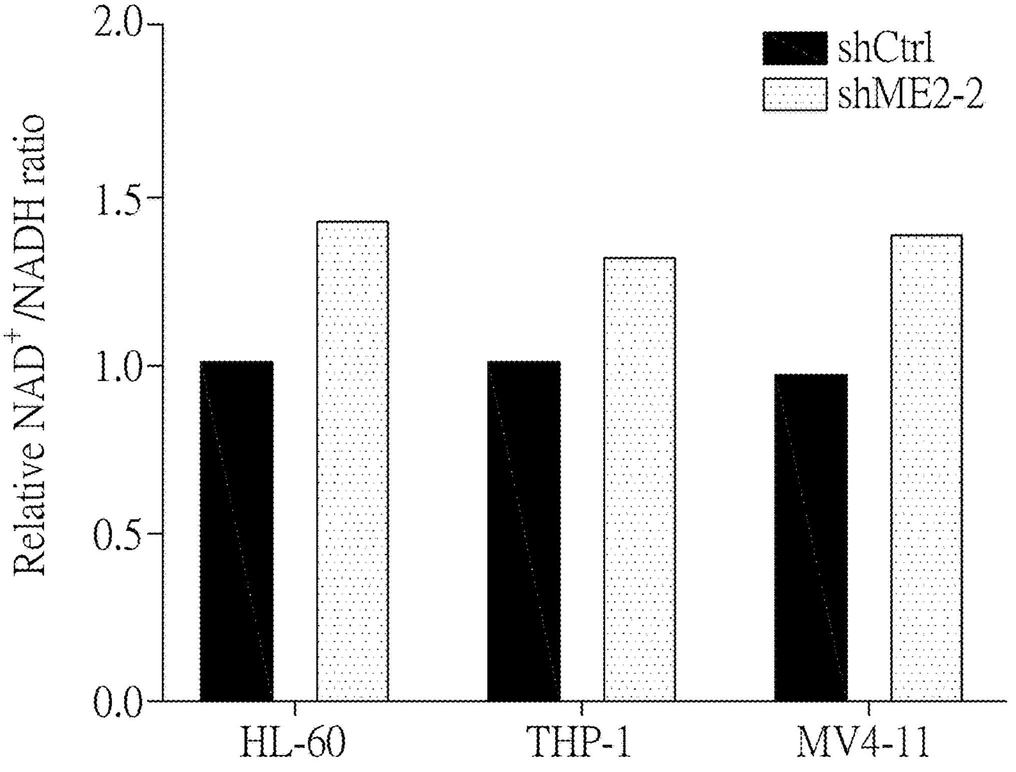
FIG. 32 shows an analysis result of the $NAD^+$/NADH ratios of AML cells whose ME2 gene has been knocked out and of normal AML cells.
Figure 33:
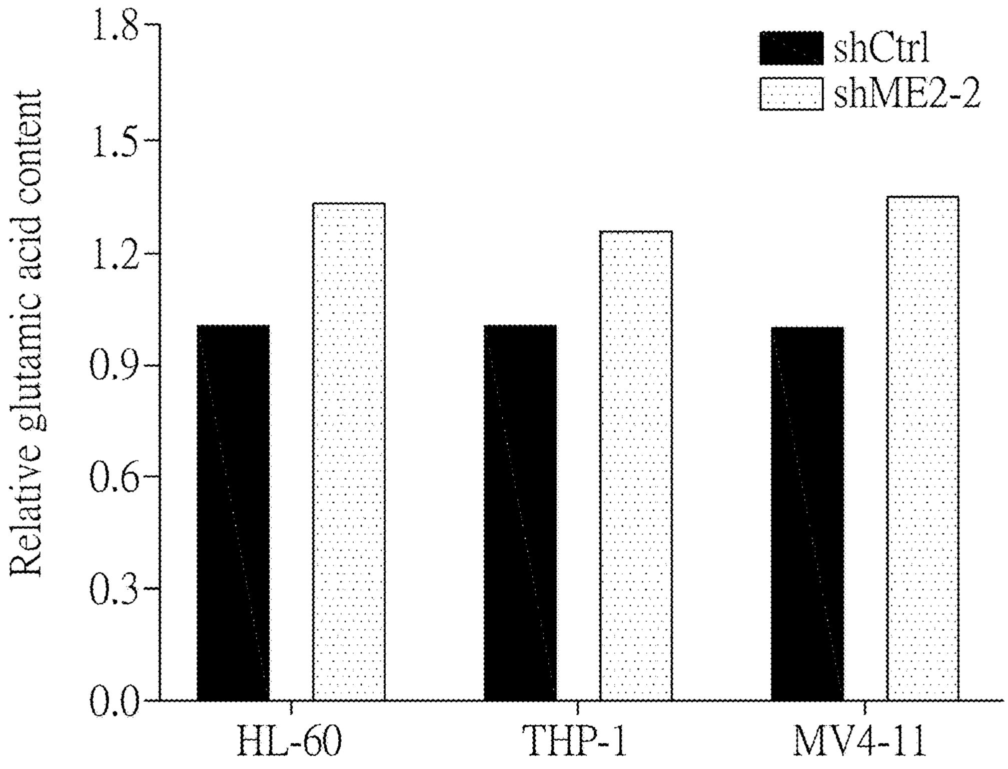
FIG. 33 shows an analysis result of the glutamic acid contents of AML cells whose ME2 gene has been knocked out and of normal AML cells.

Besides, the ATP content of each group of cells was analyzed with a commercially available cell viability assay kit (CellTiter-Glo® 2.0 Cell Viability Assay Kit), and the relative changes in ATP content of each group of cells were calculated, whose results are shown in FIG. 28. Moreover, an NAD/NADH-Glo™ assay kit, a commercially available intracellular ROS assay kit (#cat.MAK143, Sigma-Aldrich, St. Louis, MO, USA), a commercially available pyruvate colorimetric/fluorometric assay kit, and a commercially available Glutamine/Glutamate-Glo™ assay kit (#Cat. J8021; Promega, Madison, WI, USA) were used to analyze the NADPH, ROS, pyruvate, $NAD^+$, NADH, and glutamic acid contents of each group of cells, and the analysis results are shown in FIG. 29 to FIG. 33.

Figure 27:
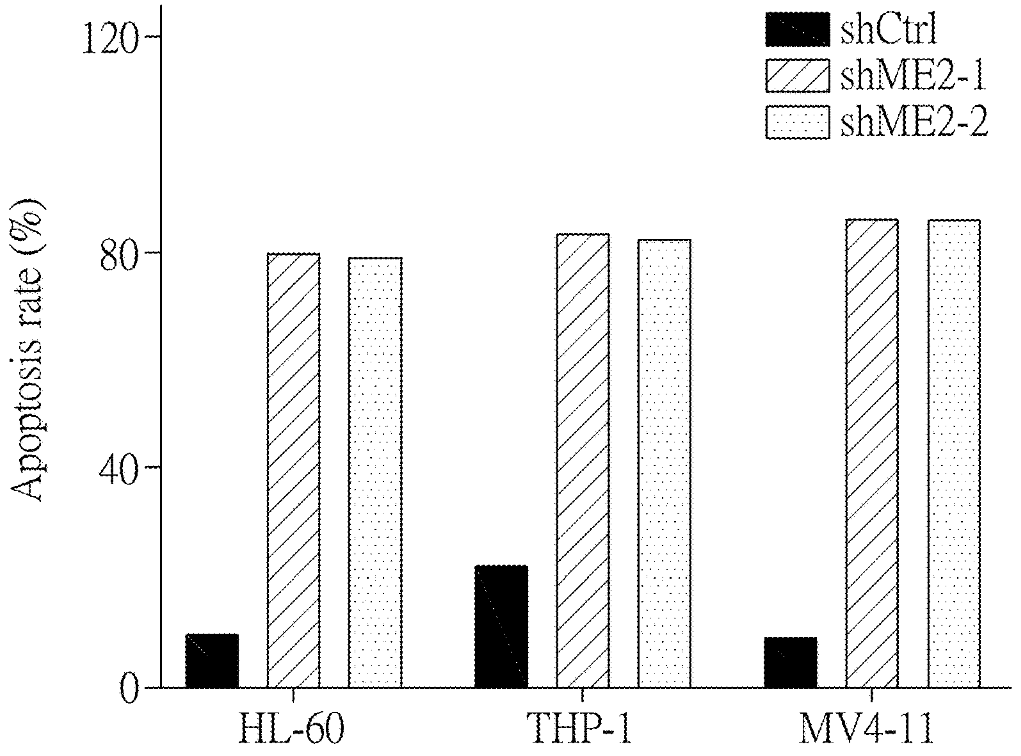
FIG. 27 shows an analysis result of the apoptosis rates of AML cells whose ME2 gene has been knocked out and of normal AML cells.

It can be inferred from the result in FIG. 27 that knockout of the ME2 gene in AML cells does lead to apoptosis of the AML cells, with the apoptosis rate being as high as 80%. This indicates that the activity of ME2 is indeed related to the growth of AML cells.

Moreover, it can be known from the results in FIG. 28 to FIG. 33 that the amounts of the ATP and NADPH generated in, and the pyruvate and NADH contents of, those HL-60, THP-1, and MV4-11 cells in which the ME2 gene had been knocked out were significantly lower than those of the control-group cells, and that the intracellular ROS contents and $NAD^+$/NADH ratios of the former cells were higher than those of the latter cells. This indicates that knockout of the ME2 gene does have a certain impact on the metabolism of AML cells and will eventually lead the AML cells to apoptosis. The foregoing results have also verified that the occurrence and progression of human acute myeloid leukemia are highly related to the expression of ME2.

Example 10: Analysis of the Effect of $Na_2EA$ on AML Cells

Through a cell survival assay, the $IC_{50}$ value of $Na_2EA$ with respect to HL-60 cells, THP-1 cells, and MV4-11 cells was found to be about 120 μM. In the following assay, therefore, the NazEA dosage of 150 μM was used.

Figure 34:
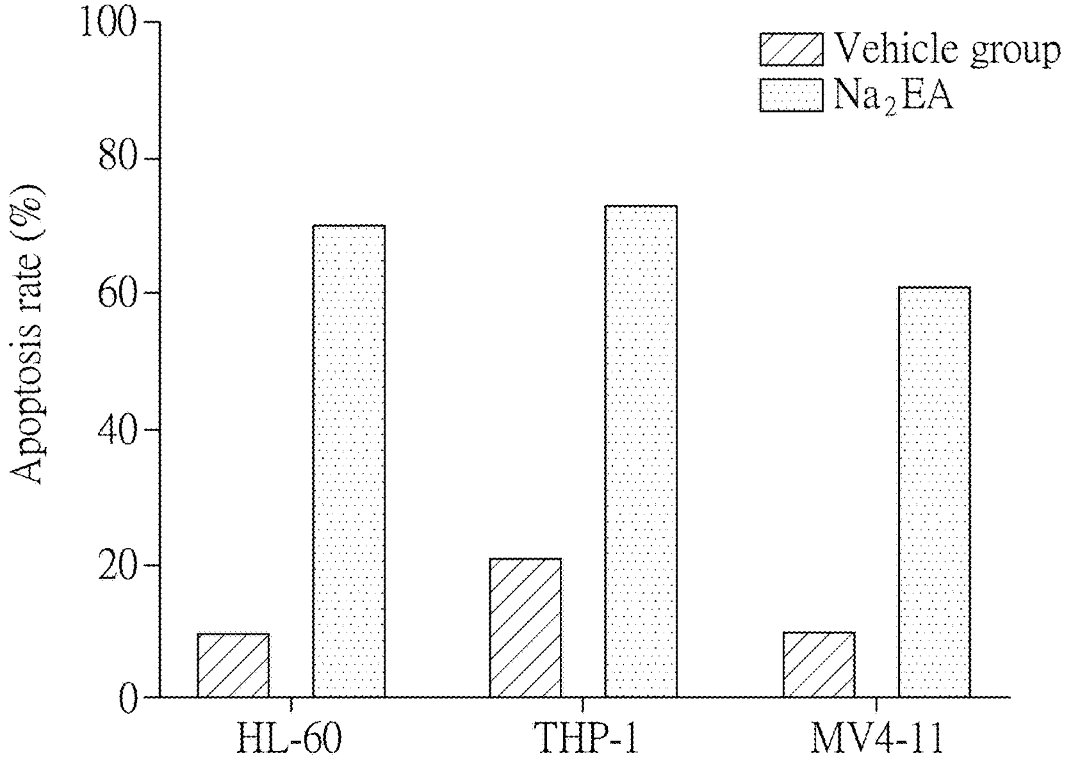
FIG. 34 shows an analysis result of the apoptosis rates of HL-60 cells, THP-1 cells, and MV4-11 cells after treatment with $Na_2EA$.
Figure 35:
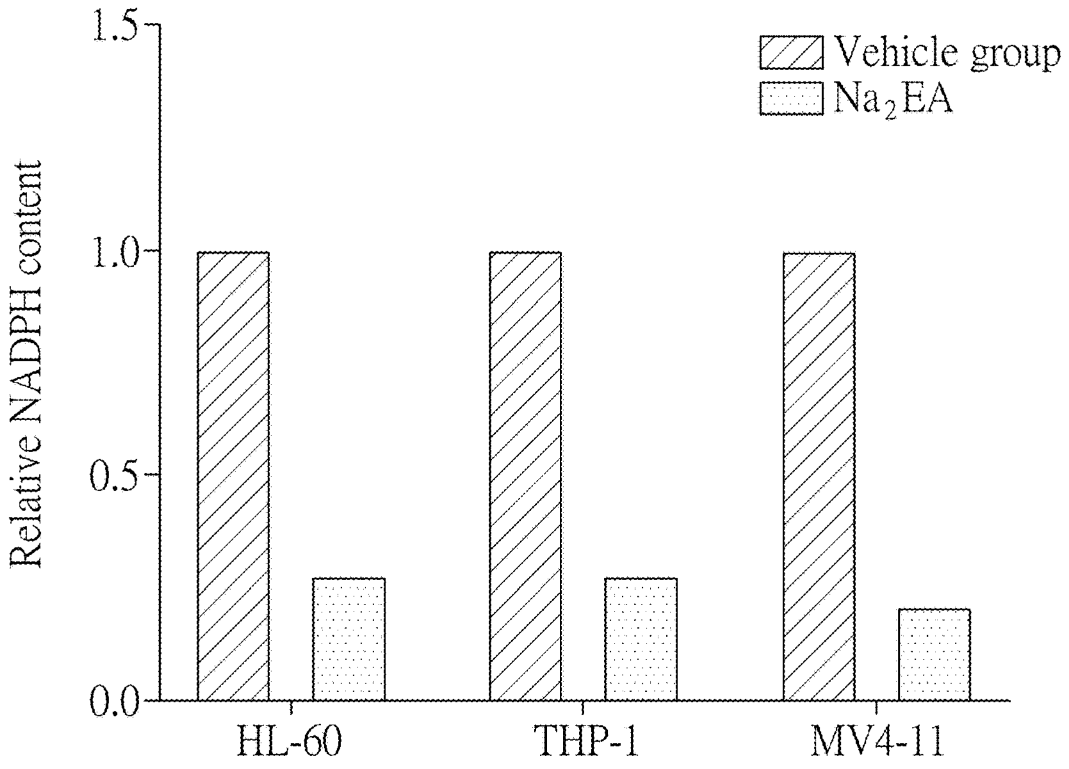
FIG. 35 shows an analysis result of the NADPH contents of HL-60 cells, THP-1 cells, and MV4-11 cells after treatment with $Na_2EA$.
Figure 36:
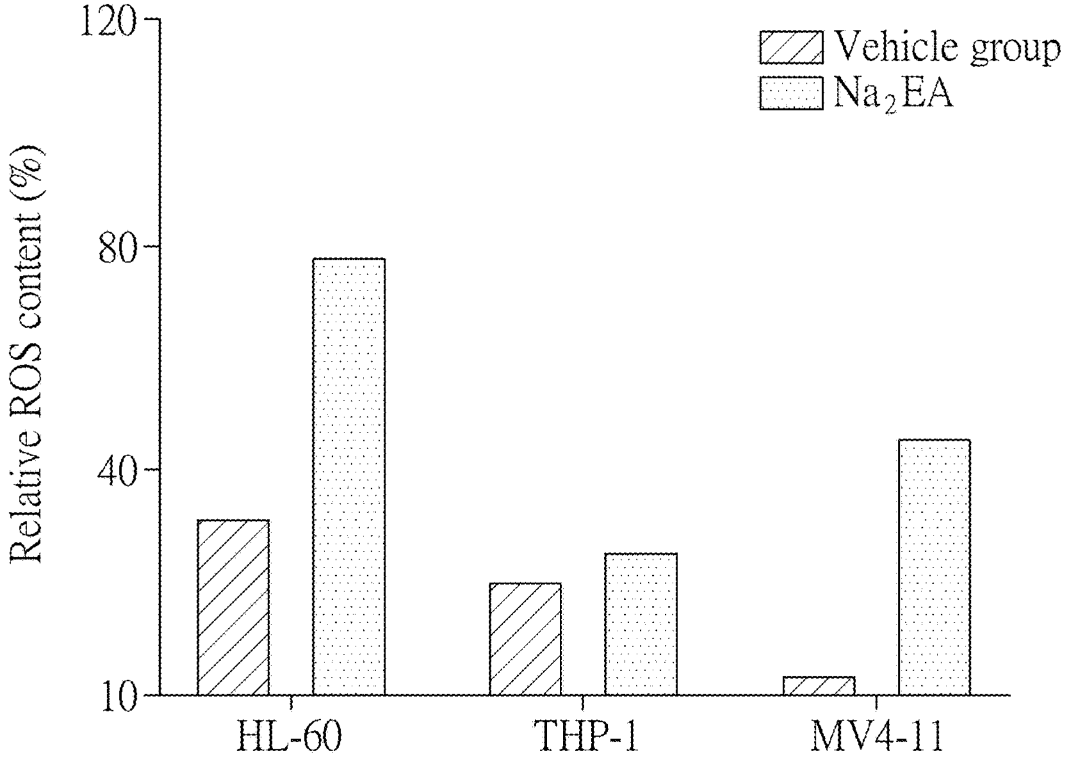
FIG. 36 shows an analysis result of the ROS contents of HL-60 cells, THP-1 cells, and MV4-11 cells after treatment with $Na_2EA$.
Figure 37:
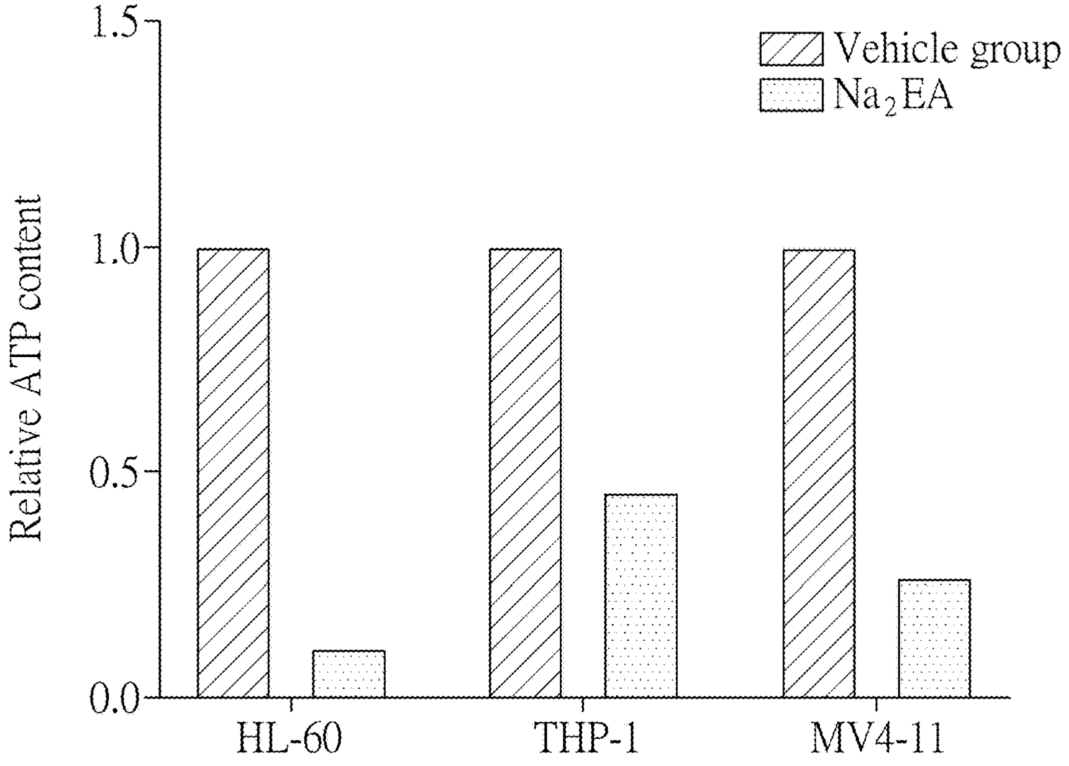
FIG. 37 shows an analysis result of the ATP contents of HL-60 cells, THP-1 cells, and MV4-11 cells after treatment with $Na_2EA$.

HL-60 cells, THP-1 cells, and MV4-11 cells were each divided into two groups, namely a vehicle group to be cultured in an RPMI culture medium and a group to be cultured in an RPMI culture medium containing 150 μM $Na_2EA$. After culturing for 24 hours, the culture media were renewed. After culturing for another 48 hours, a commercially available apoptosis detection kit (Annexin V Apoptosis Detection Kit) and flow cytometer were used to analyze the apoptosis rates of the cells, and the results are shown in FIG. 34. In addition, a commercially available cell viability assay kit (CellTiter-Glo® 2.0 Cell Viability Assay Kit), a NAD/NADH-Glo™ assay kit, a commercially available intracellular ROS assay kit (#cat.MAK143, Sigma-Aldrich, St. Louis, MO, USA), and a commercially available pyruvate colorimetric/fluorometric assay kit were used to analyze the NADPH, ROS, and ATP contents of each group of cells, and the results are shown in FIG. 35 to FIG. 37.

Figure 38:
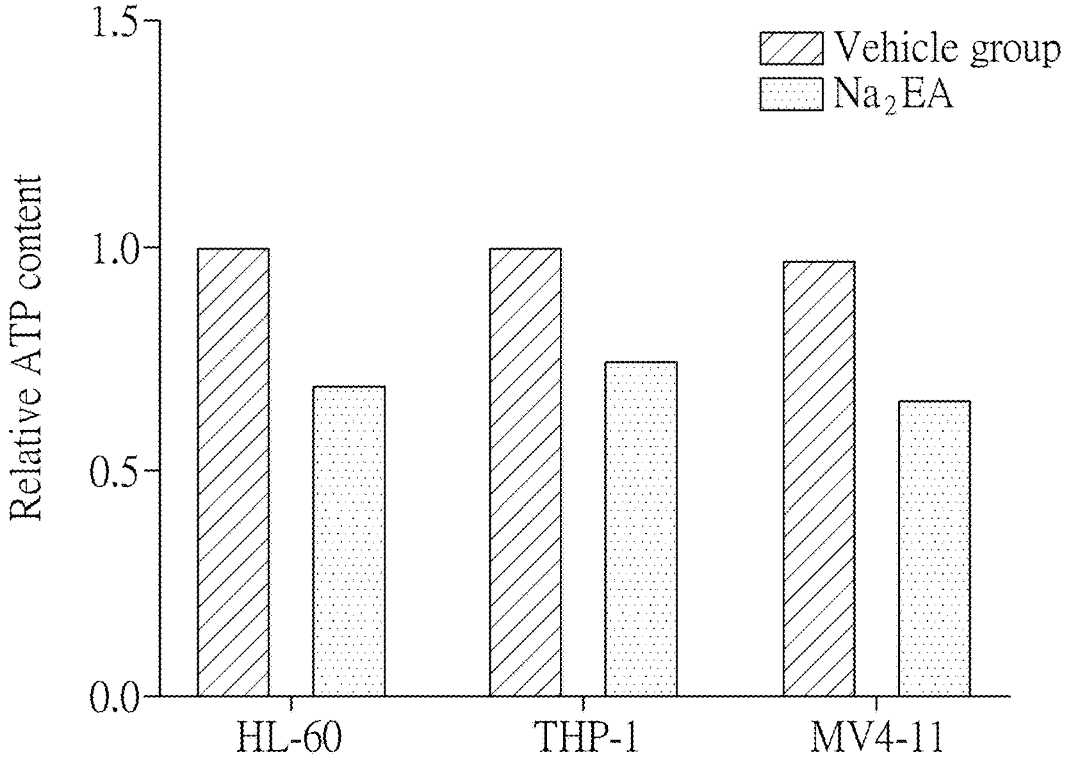
FIG. 38 shows a quantification result of HL-60 cells, THP-1 cells, and MV4-11 cells after staining with ATP-Red Live Cell Dye.
Figure 39:
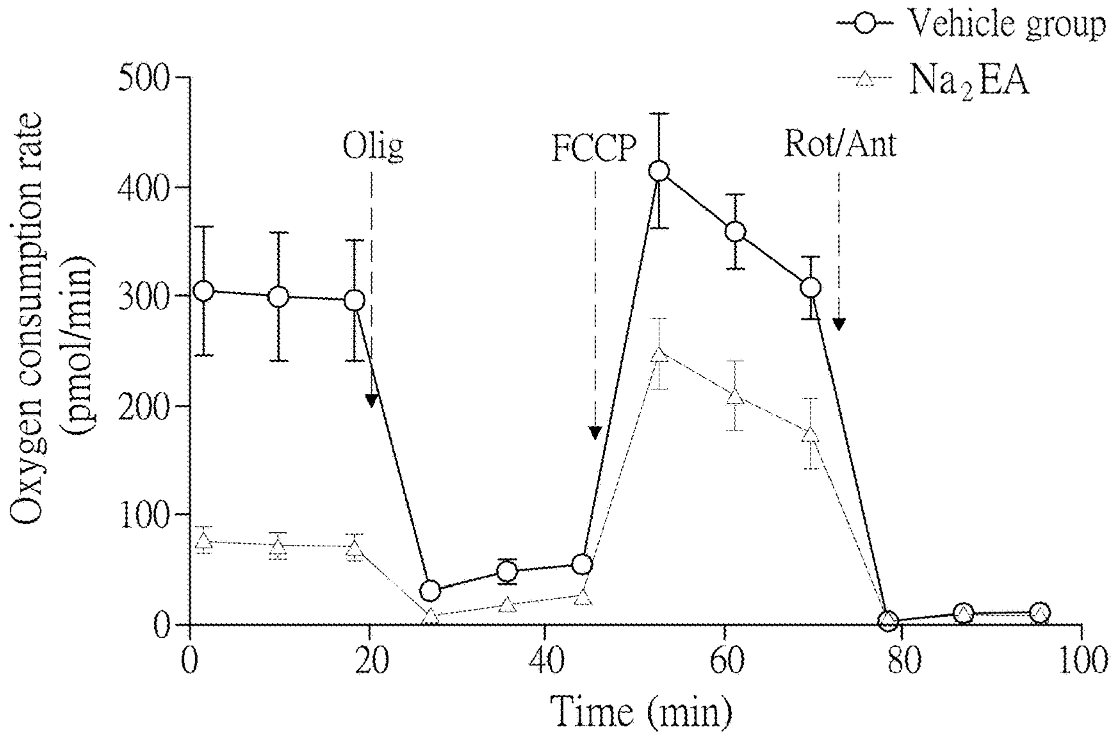
FIG. 39 shows an analysis result of the oxygen consumption rates of HL-60 cells.
Figure 40:
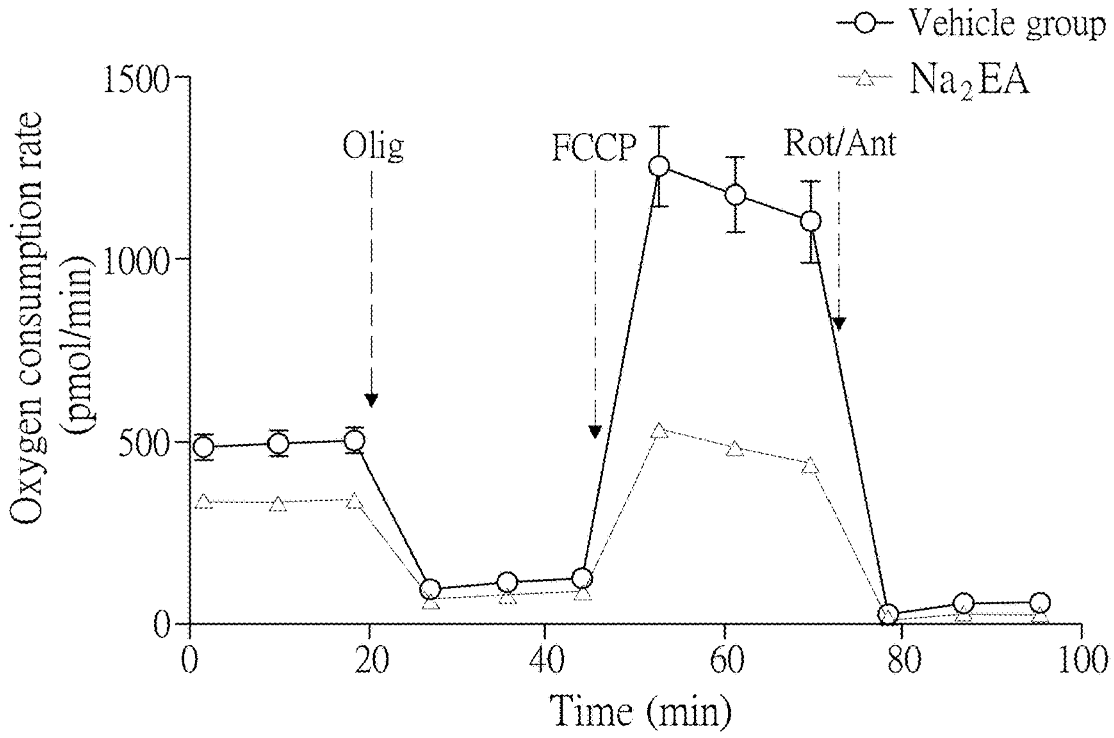
FIG. 40 shows an analysis result of the oxygen consumption rates of THP-1 cells.
Figure 41:
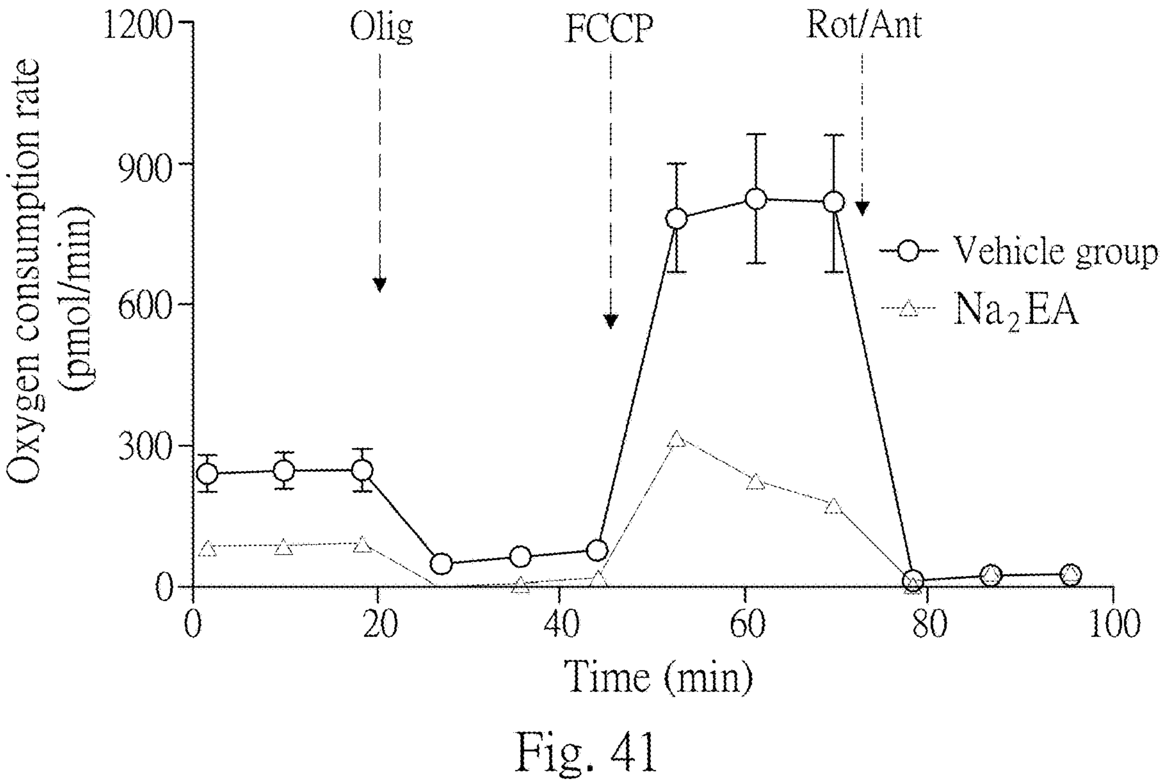
FIG. 41 shows an analysis result of the oxygen consumption rates of MV4-11 cells.
Figure 42:
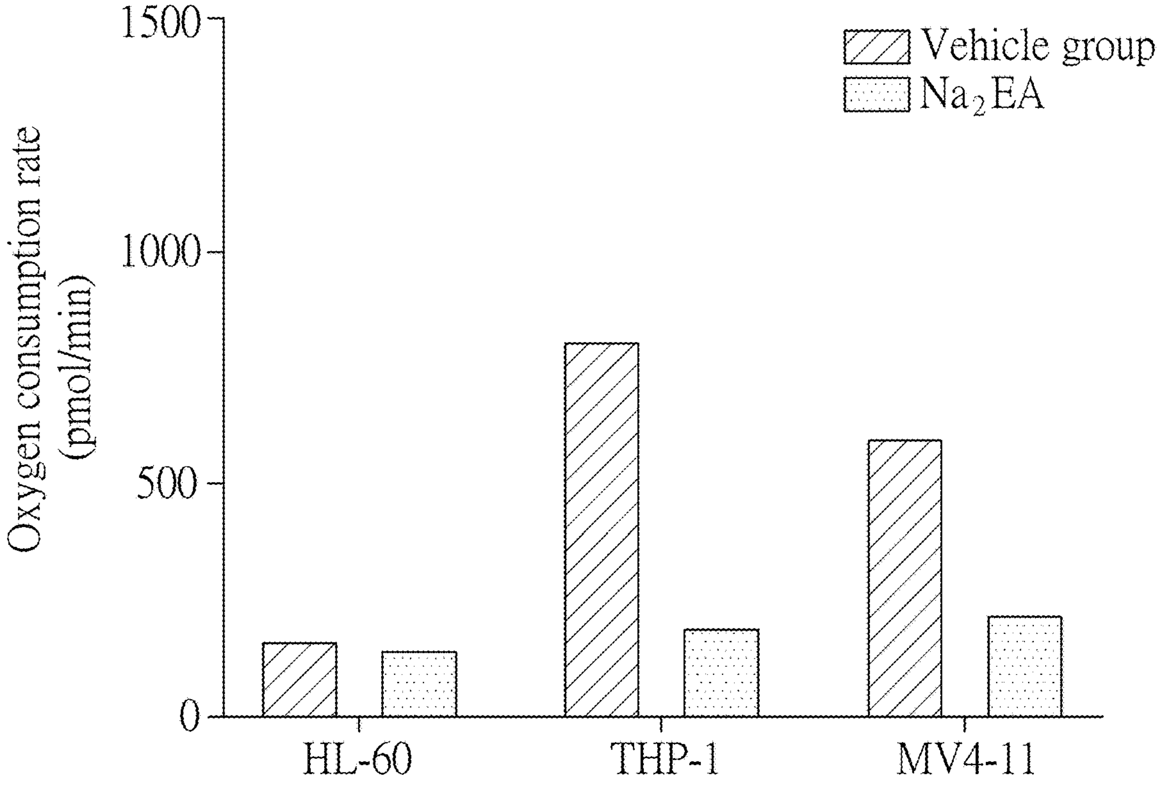
FIG. 42 shows an analysis result of the spare respiratory capacity of HL-60 cells, THP-1 cells, and MV4-11 cells.
Figure 43:
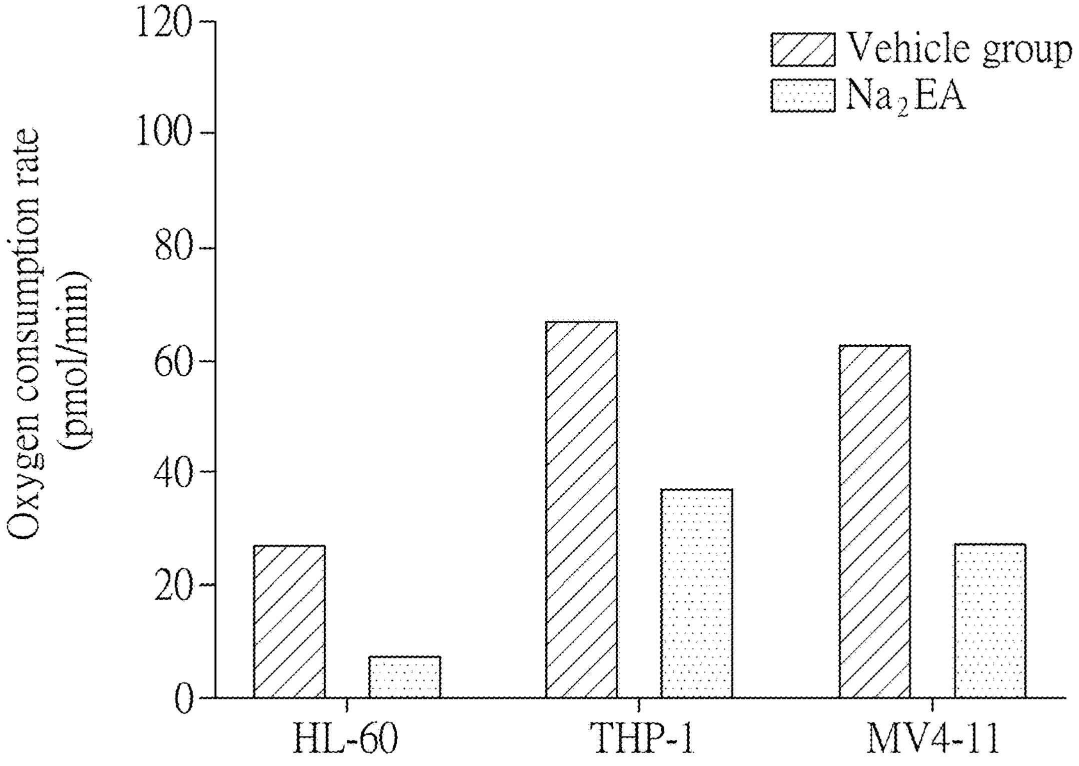
FIG. 43 shows an analysis result of proton leak from HL-60 cells, THP-1 cells, and MV4-11 cells.
Figure 44:
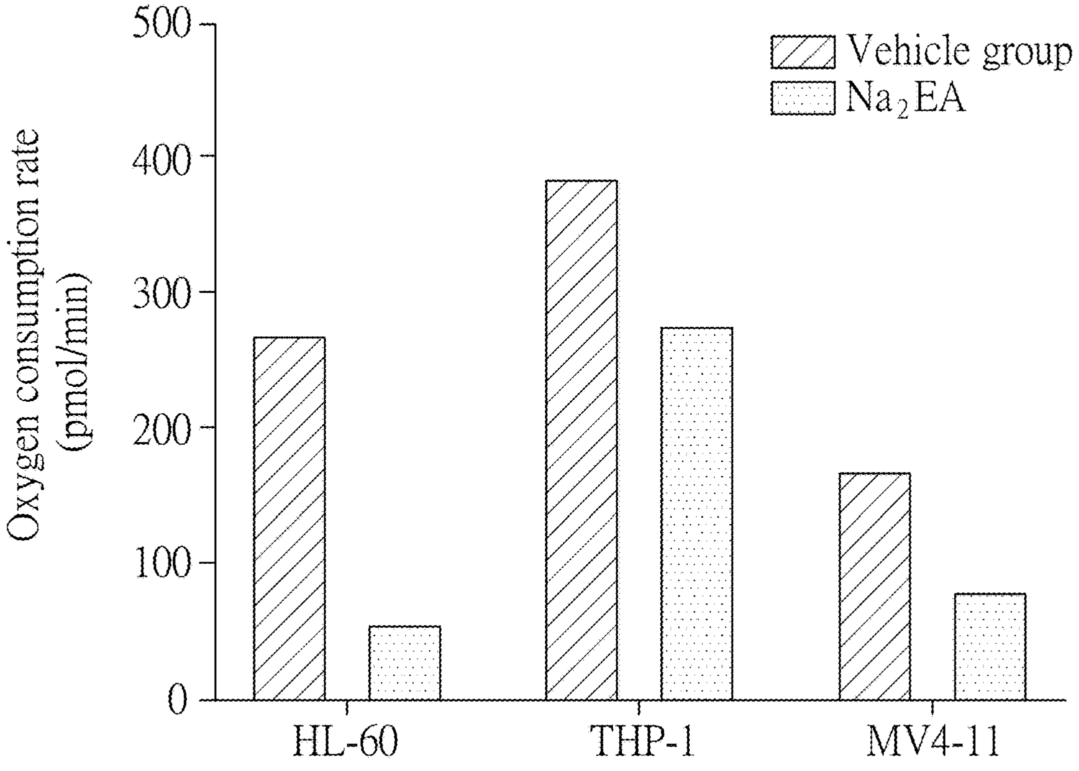
FIG. 44 shows an analysis result of the generation of ATP by the mitochondrial electron transport chains in HL-60 cells, THP-1 cells, and MV4-11 cells.
Figure 45:
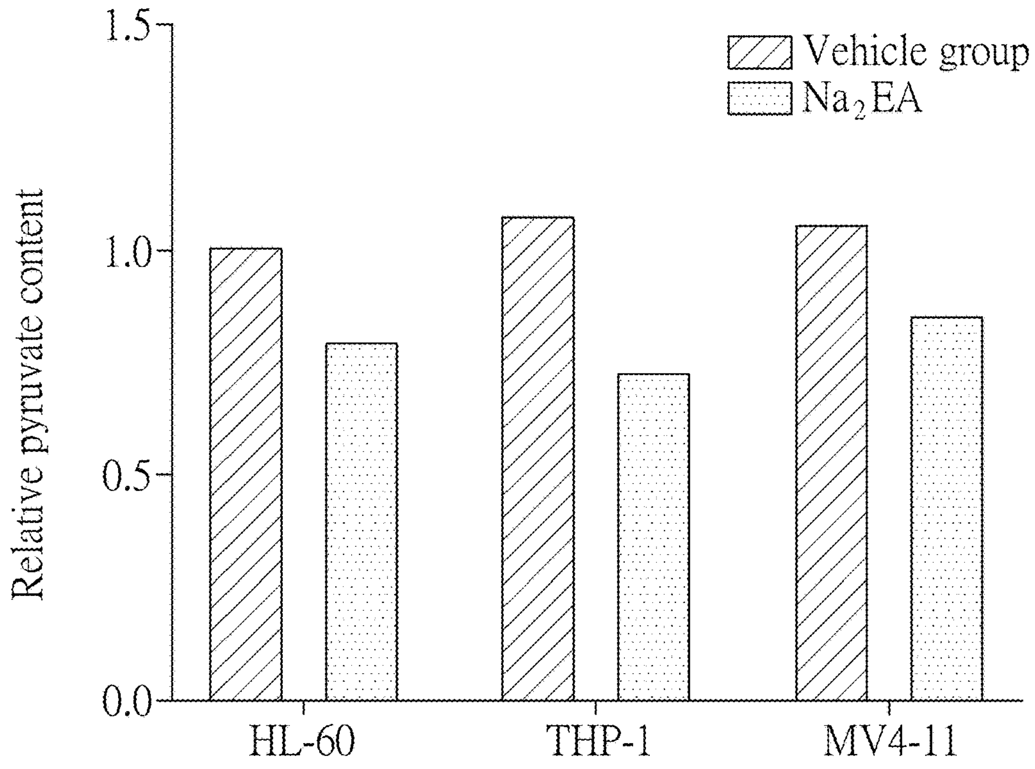
FIG. 45 shows an analysis result of the pyruvate contents of HL-60 cells, THP-1 cells, and MV4-11 cells.
Figure 46:
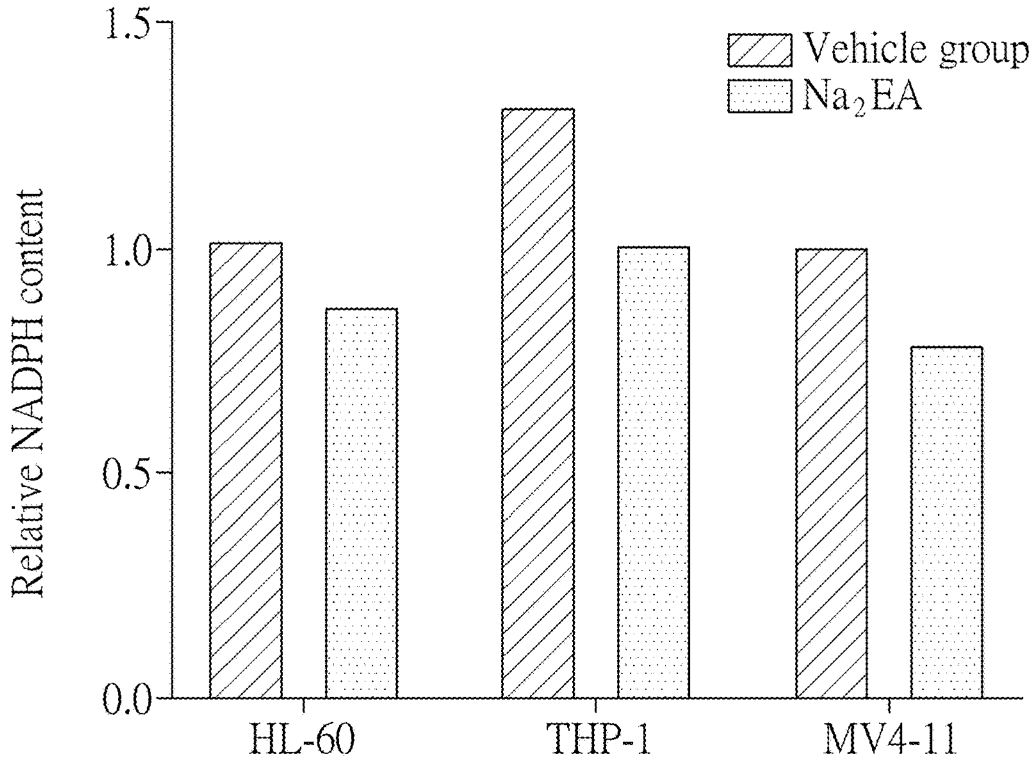
FIG. 46 shows an analysis result of the NADH contents of HL-60 cells, THP-1 cells, and MV4-11 cells.
Figure 47:
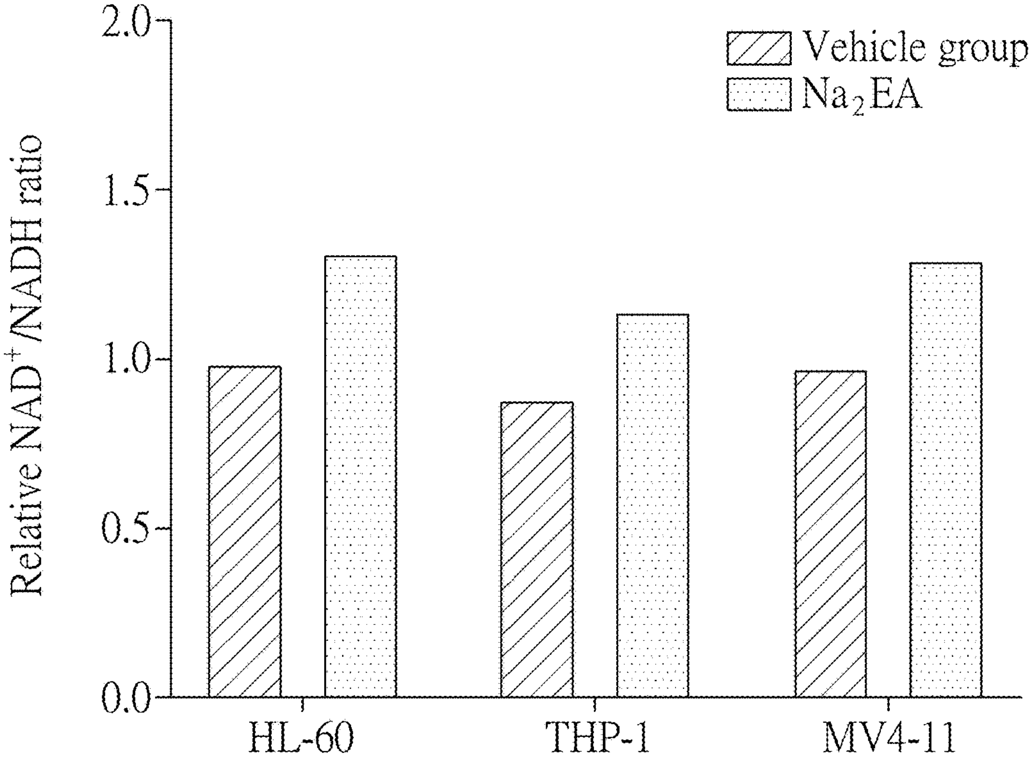
FIG. 47 shows an analysis result of the $NAD^+$/NADH ratios of HL-60 cells, THP-1 cells, and MV4-11 cells.
Figure 48:
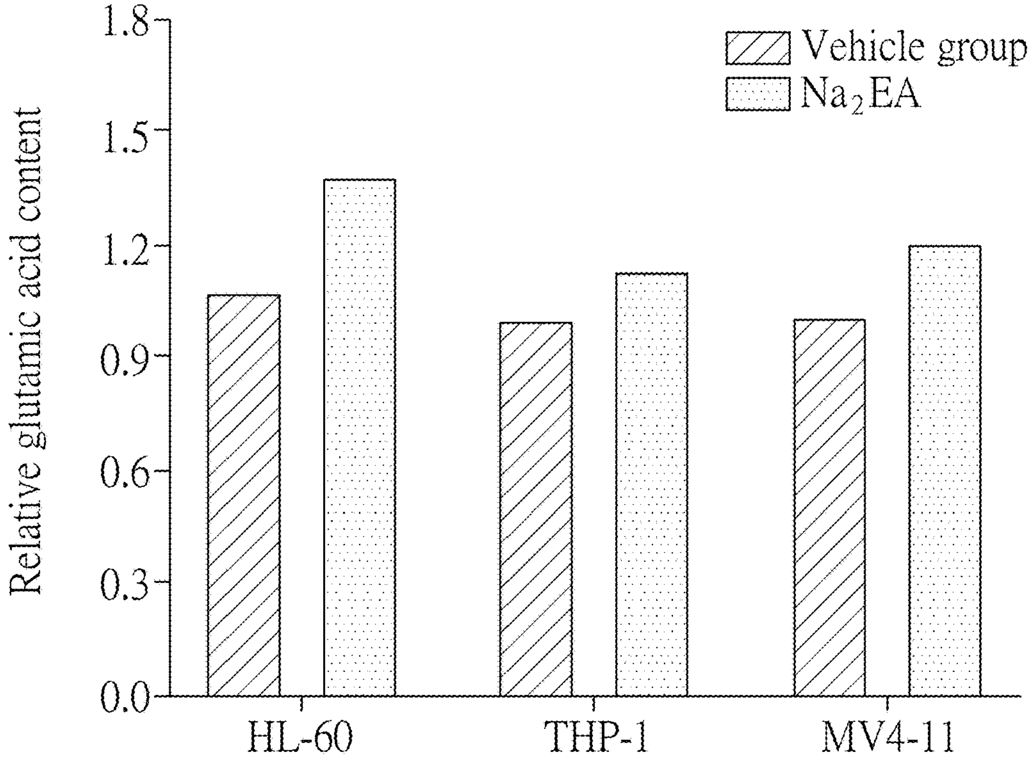
FIG. 48 shows an analysis result of the relative glutamic acid contents of HL-60 cells, THP-1 cells, and MV4-11 cells.

Furthermore, the cells in each group were stained with ATP-Red Live Cell Dye (BioTracker™ ATP-Red Live Cell Dye) and were observed and quantified under a fluorescence microscope, with the quantification results shown in FIG. 38. The oxygen consumption rate of each group of cells was also determined in the same way as in example 6, with the introduction of different stress testing conditions, and the results are shown in FIG. 39 to FIG. 44.

Besides, the NADH, pyruvate, $NAD^+$, NADH, and glutamic acid contents of each group of cells were analyzed with a NAD/NADH-Glo™ assay kit, a commercially available pyruvate colorimetric/fluorometric assay kit, and a commercially available Glutamine/Glutamate-Glo™ assay kit (#Cat. J8021; Promega, Madison, WI, USA) in the same way as in example 9, and the results are shown in FIG. 45 to FIG. 48.

It can be inferred from the result in FIG. 34 that NazEA can induce the apoptosis of at least 60-75% of each of HL-60 cells, THP-1 cells, and MV4-11 cells. It can be further inferred from the results in FIG. 35 to FIG. 38 that after treatment with $Na_2EA$ to inhibit the expression of ME2 in HL-60 cells, THP-1 cells, and MV4-11 cells, the NADPH and ATP contents of those AML cells will be greatly reduced, and the steady state of ROS destroyed, such that growth of the AML cells is inhibited. The results in FIG. 39 to FIG. 44 also show that the oxygen consumption rates of the AML cells, mitochondrial proton leak from the AML cells, and the yield of ATP by the mitochondrial electron transport chains in the AML cells were lowered because of the presence of NazEA.

Moreover, it can be inferred from the results in FIG. 45 to FIG. 48 that the energy metabolism of those AML cells cultured in a $Na_2EA$-containing environment was inhibited (i.e., with the pyruvate and NADH contents of the AML cells reduced, and the $NAD^+$/NADH ratios and glutamic acid contents increased) because of the ability of NazEA to silence, or inhibit the expression of, ME2.

The foregoing results indicate that $Na_2EA$ is indeed capable of inhibiting the growth, and causing apoptosis, of AML cells and thereby producing the effect of treating, or slowing down the progression of, human acute myeloid leukemia.

Example 11: Mass Spectrometric Analysis

The $Na_2EA$-treated HL-60 cells ($1\times10^7$ cells) and the HL-60 cells untreated with NazEA ($1\times10^7$ cells) in example 10 were taken, added into 1 mL of 80% methanol, and centrifuged at 4° C. and 12,000×g for 10 minutes. After the supernatants were evaporated with nitrogen gas, an analysis was performed using a Waters ultra-high performance liquid chromatograph coupled with Waters Xevo TQ-S MS (Waters Corp. Milford, MA, USA). The analysis results are shown in FIG. 49A and FIG. 49B.

Figure 49A:
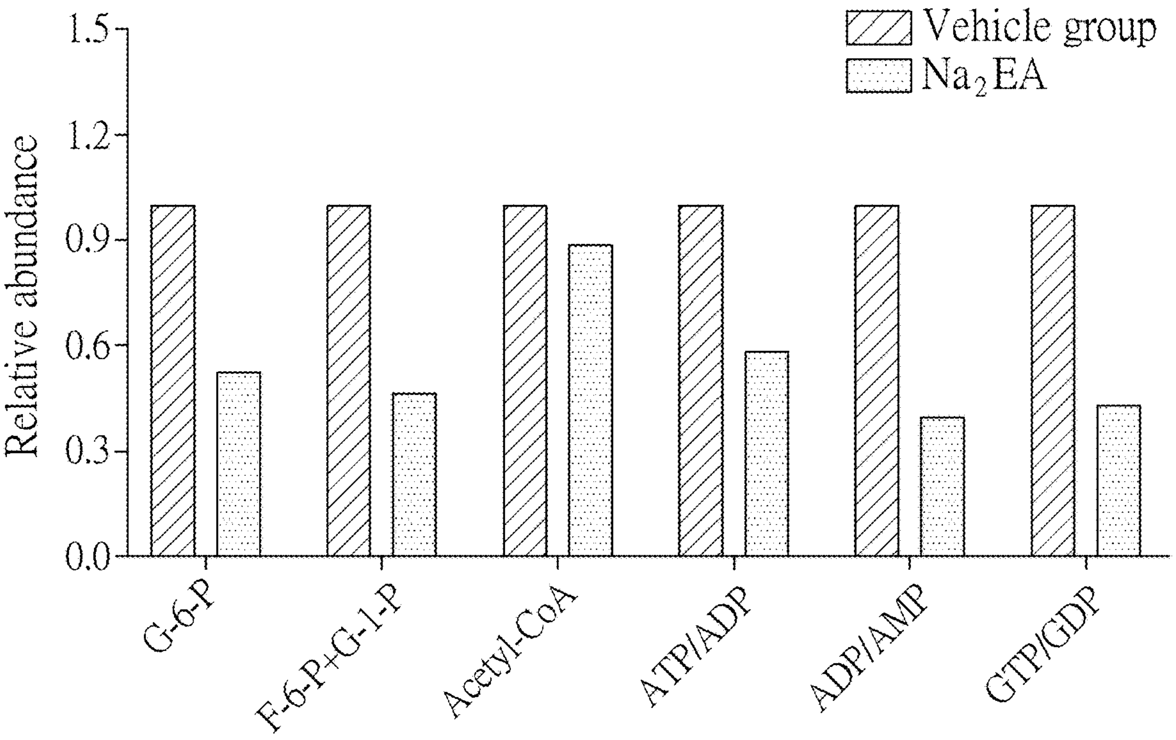
FIG. 49A shows a mass spectrometric analysis result of changes in the intermediates in HL-60 cells that participated in energy metabolism.
Figure 49B:
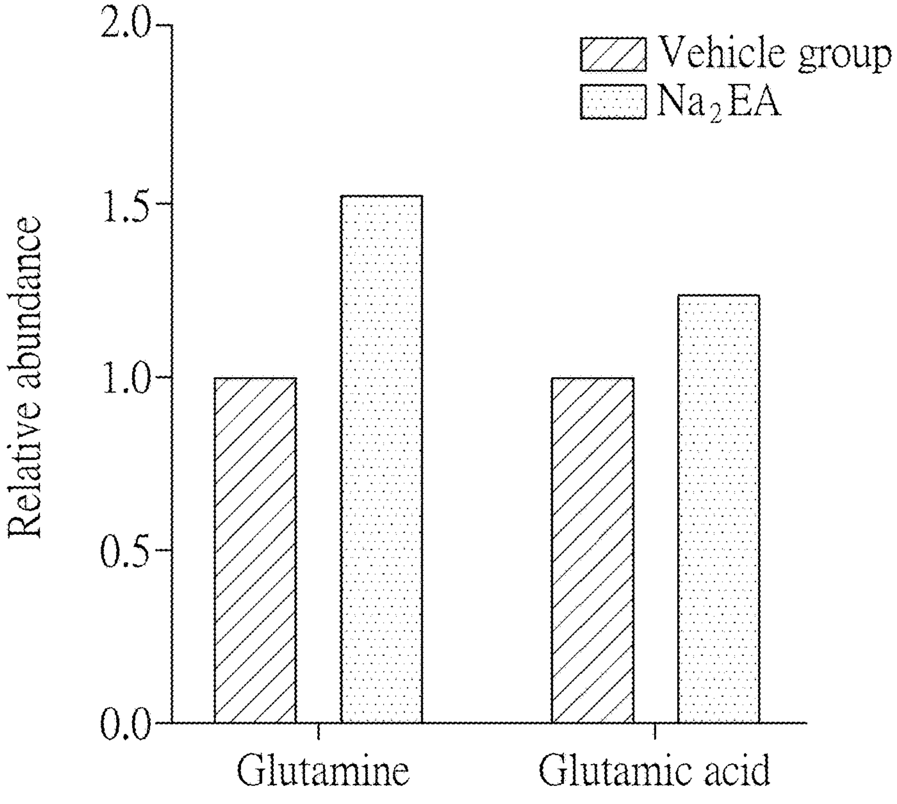
FIG. 49B shows a mass spectrometric analysis result of changes in the intermediates in HL-60 cells that participated in glutamic acid metabolism.
Figure 50A:
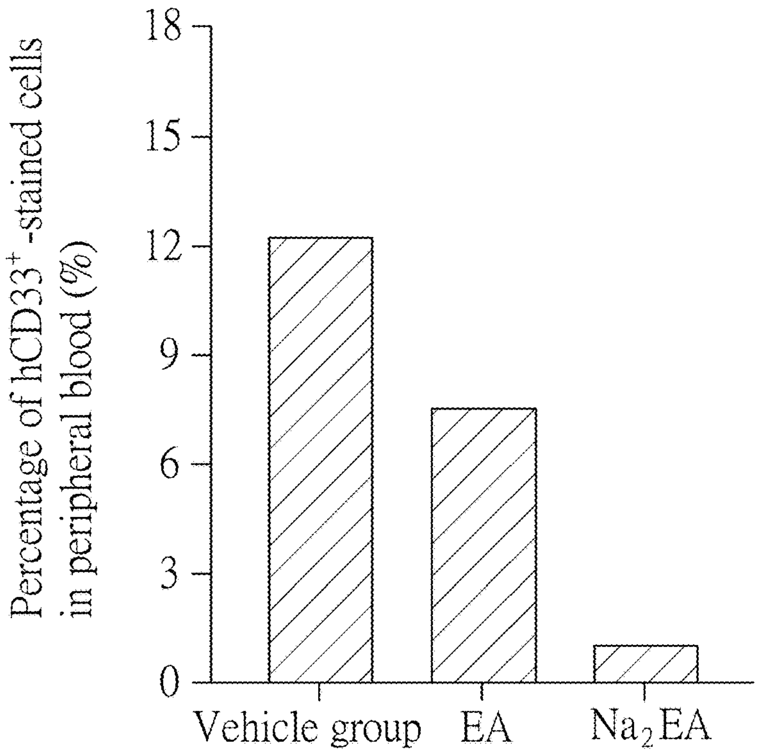
FIG. 50A shows the percentages of $CD33^+$-stained cells in the peripheral blood of mice transplanted with differently treated THP-1 cells.
Figure 50B:
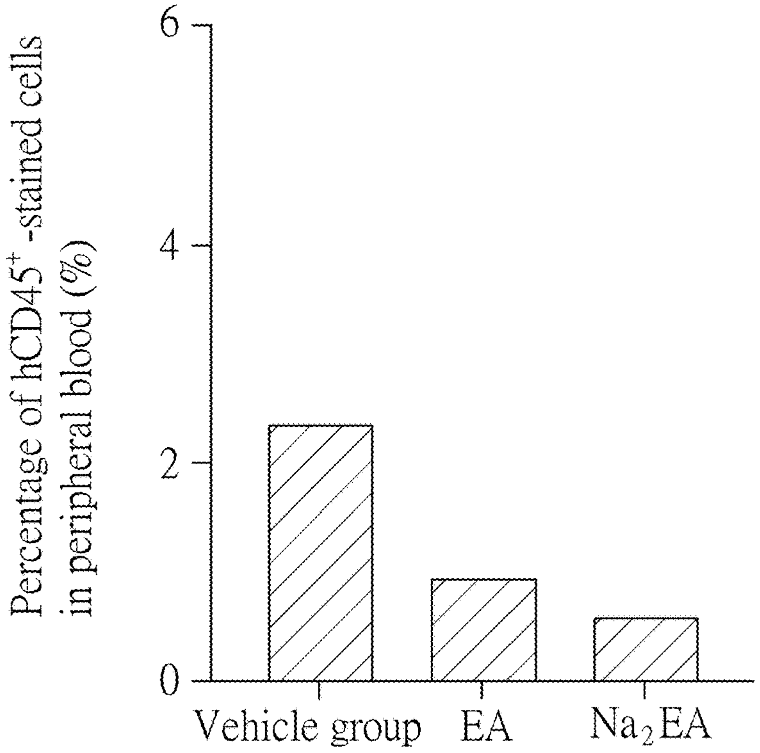
FIG. 50B shows the percentages of $CD45^+$-stained cells in the peripheral blood of mice transplanted with differently treated THP-1 cells.
Figure 51A:
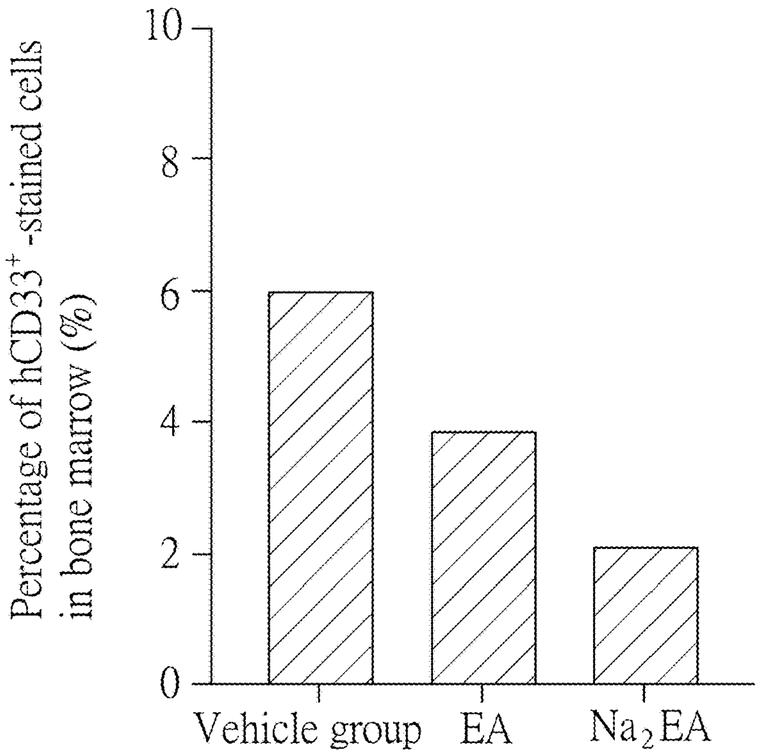
FIG. 51A shows the percentages of $CD33^+$-stained cells in the bone marrow of mice transplanted with differently treated THP-1 cells.
Figure 51B:
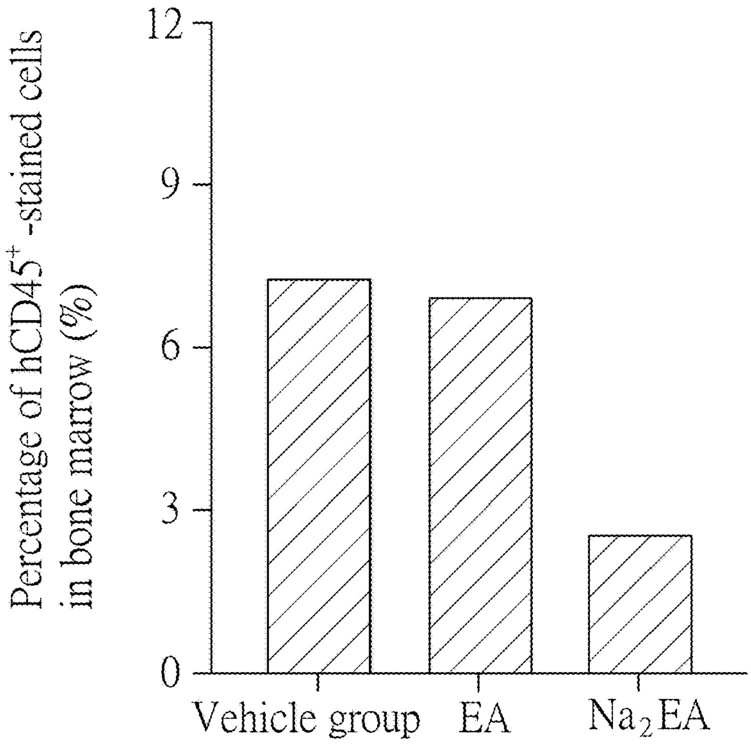
FIG. 51B shows the percentages of $CD45^+$-stained cells in the bone marrow of mice transplanted with differently treated THP-1 cells.
Figure 52A:
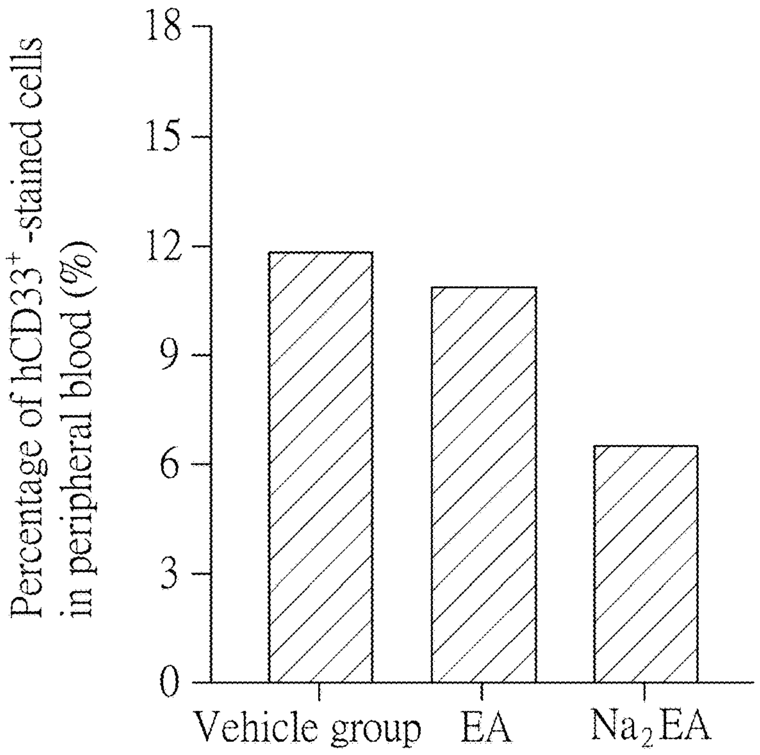
FIG. 52A shows the percentages of $CD33^+$-stained cells in the peripheral blood of mice transplanted with differently treated MV4-11 cells.
Figure 52B:
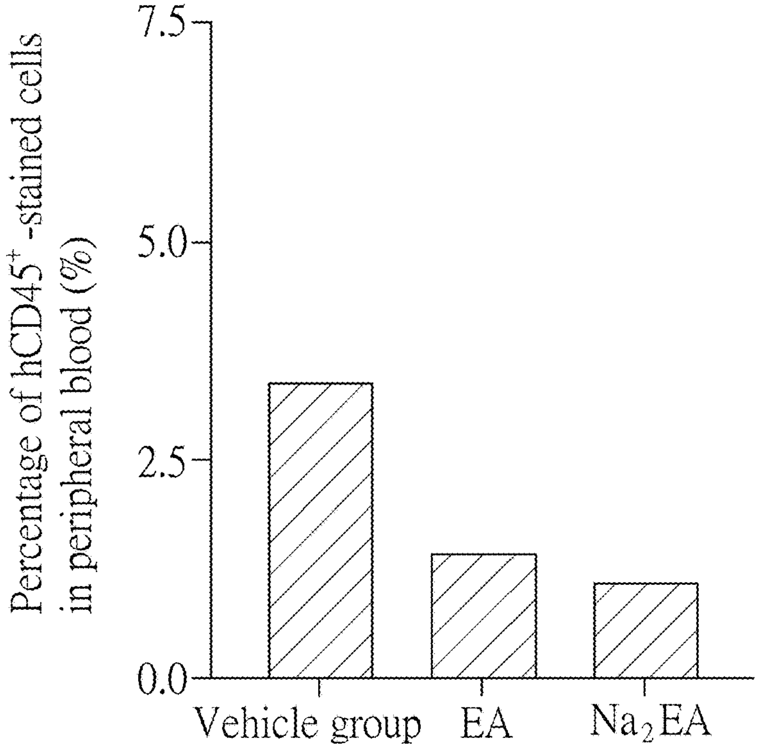
FIG. 52B shows the percentages of $CD45^+$-stained cells in the peripheral blood of mice transplanted with differently treated MV4-11 cells.
Figure 53A:
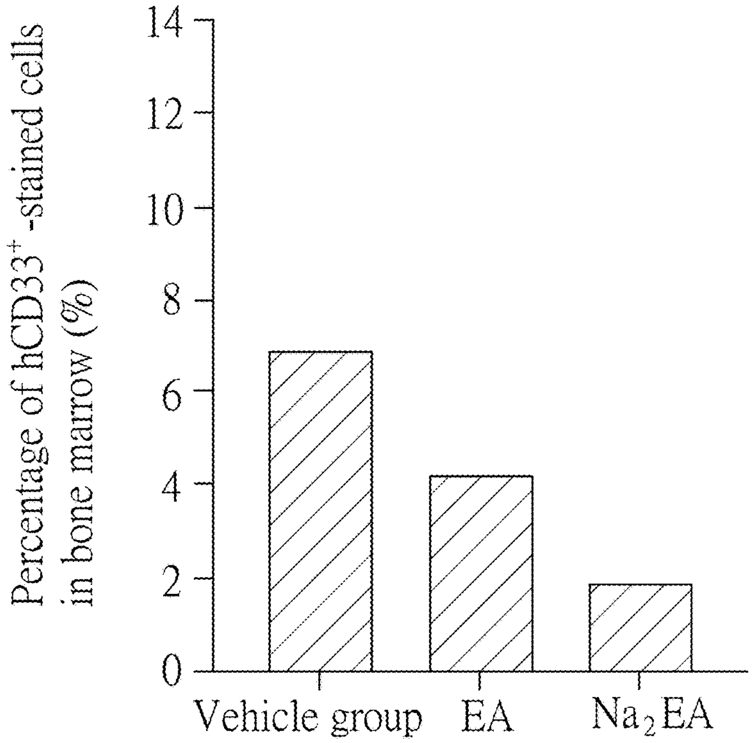
FIG. 53A shows the percentages of $CD33^+$-stained cells in the bone marrow of mice transplanted with differently treated MV4-11 cells.
Figure 53B:
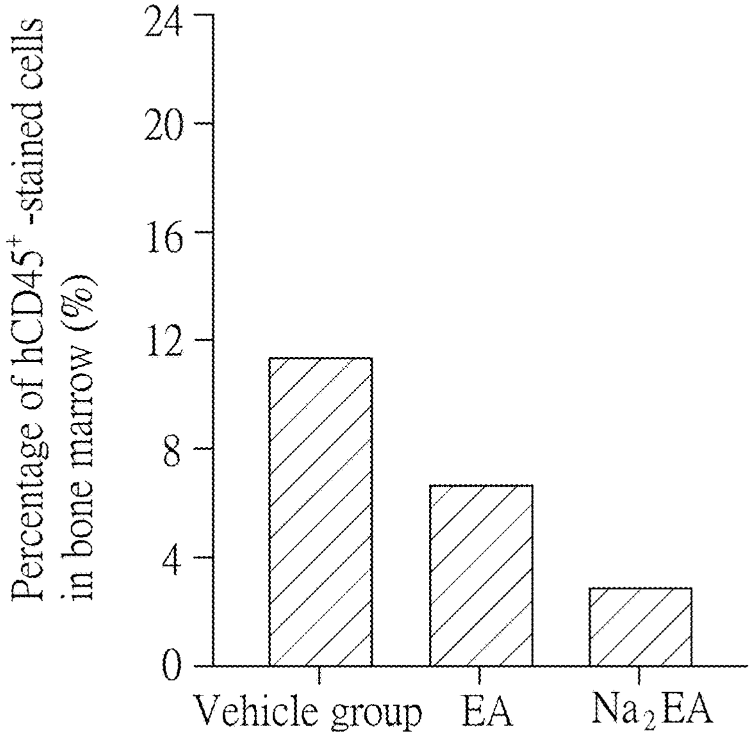
FIG. 53B shows the percentages of $CD45^+$-stained cells in the bone marrow of mice transplanted with differently treated MV4-11 cells.

It can be inferred from the results in FIG. 49A and FIG. 49B that $Na_2EA$ can suppress the glucose-6-phosphate (G-6-P) content, the fructose-6-phosphate (F-6-P) content, and the glucose-1-phosphate (G-1-P) content while increasing the glutamic acid content and the glutamine content. That is to say, $Na_2EA$ can render ME2 incapable of participating in or regulating the glycolysis reaction and the metabolism of glutamic acid.

Example 12: Animal Test

A plurality of 8-week-old ASID mice (or mice with advanced severe immunodeficiency, or more specifically NOD.Cg-Prkde$^{scid}$Il2rg$^{tm1\,Wjl}$/YckNarl mice) were randomly divided into 6 groups. Each group of mice was intravenously injected with one of a plurality of differently treated AML cell variants at a frequency of 5 days per week for 4 weeks. The AML cell variants injected into the 6 groups of mice are as follows:

Group 1-1: THP-1 cells

Group 2-1: THP-1 cells with EA (at a dosage of 4 mg/kg)

Group 3-1: THP-1 cells with $Na_2EA$ (at a dosage of 4 mg/kg)

Group 1-2: MV4-11 cells

Group 2-2: MV4-11 cells with EA (at a dosage of 4 mg/kg)

Group 3-2: MV4-11 cells with $Na_2EA$ (at a dosage of 4 mg/kg)

On the 21$^{st}$ day of the test, peripheral blood was collected from the submandibular vein of the mice, and bone marrow was collected as well. The blood and bone marrow were stained with specific markers (CD33 and CD45) and then reacted with a fluorescent antibody, before the CD33+ or CD45$^{+}$-stained cells were quantified with a flow cytometer. The results are shown in FIG. 50 to FIG. 53.

It can be inferred from the results in FIG. 50 to FIG. 53 that the administration of either EA or $Na_2EA$ can reduce the AML cells in mice, and that $Na_2EA$ is more effective in reducing AML cells than EA.

What is claimed is:

1. A method for treating acute myeloid leukemia using a human mitochondrial malic enzyme 2 inhibitor, comprising: administering an effective amount of a small-molecule compound or of a salt thereof to a cancer patient, wherein the small-molecule compound is 4,4'-methylene-bis(3-hydroxy-2-naphthoic acid) or 5,5'-methylenedisalicylic acid.

2. The method for treating acute myeloid leukemia using a human mitochondrial malic enzyme 2 inhibitor as claimed in claim 1, wherein the salt of the small-molecule compound is a sodium salt of 4,4'-methylene-bis(3-hydroxy-2-naphthoic acid).

3. The method for treating acute myeloid leukemia using a human mitochondrial malic enzyme 2 inhibitor as claimed in claim 1, wherein the small-molecule compound or the salt thereof is used to inhibit metastasis of the cancer.

4. The method for treating acute myeloid leukemia using a human mitochondrial malic enzyme 2 inhibitor as claimed in claim 1, wherein the small-molecule compound or the salt thereof binds to a human mitochondrial NAD (P)$^{+}$-dependent malic enzyme 2 in a cancer cell to form a complex and thereby inhibit activity of the human mitochondrial NAD (P)$^{+}$-dependent malic enzyme 2.

* * * * *